United States Patent [19]
Wu et al.

[11] Patent Number: 6,046,030
[45] Date of Patent: Apr. 4, 2000

[54] HUMAN LIG-1 HOMOLOG (HLIG-1)

[75] Inventors: Shujian Wu, Levittown; Raymond W Sweet, Bala Cynwyd; Alemseged Truneh, West Chester, all of Pa.

[73] Assignee: SmithKline Beecham Corporation, Philadelphia, Pa.

[21] Appl. No.: 08/986,485

[22] Filed: Dec. 8, 1997

Related U.S. Application Data

[60] Provisional application No. 60/059,448, Sep. 22, 1997.

[51] Int. Cl.⁷ .......................... C12N 15/12; C12N 15/85; C12N 15/63; C07H 21/04
[52] U.S. Cl. ................... 435/69.1; 435/320.1; 435/325; 536/23.1; 536/23.5
[58] Field of Search ................. 536/23.1, 23.5; 435/69.1, 320.1, 325

[56] References Cited

PUBLICATIONS

GenBank Accession #D78572.
GenBank Accession #X53959.
GenBank Accession #P35859.
GenBank Accession #U11052.
GenBank Accession #X66494.
Y. Suzuki, et al., "cDNA Cloning of a Novel Membrane Glycoprotein That Is Expressed specifically in Glial Cells in the Mouse Brain", J. Biol. Chem., vol. 271, pp. 22522–22527 (1996).
J. Dai, et al., "Molecular Cloning Of The Acid–Labile Subunit Of The Rat Insulin–Like Growth Factor Binding Protein Complex", Biochem Biophys. Res. Commun., vol. 188, pp. 304–309 (1992).
J.M. Rothberg, et al., "slit: an extracellular protein necessary for development of midline glia and commissural axon pathways contains both EGF and LRR domains" Genes & Development, vol. 4, pp. 2169–2187 (1990).
R.E. Nelson et al., "Peroxidasin: a novel enzyme–matrix protein of Drosophila development", EMBO J., vol. 13, pp. 3438–3447 (1994).
W.Mayser et al., "Primary structure and functional expression of a choline transporter expressed in the rat nervous system", FEBS Lett., vol. 305, pp. 31–36 (1992).
Human Genome Sciences EST #231054.
Genbank Accession #V04445.
Lewin, *Genes IV* (1990) Oxford University Press, NY pp. 75–77.
Schlesinger (ed); George et al, "Current Methods in Sequence Comparison and Analysis" *Macromolecular Sequencing and Synthesis*, (1988) 127–149.

*Primary Examiner*—Anthony C. Caputa
*Assistant Examiner*—Stephen Gucker
*Attorney, Agent, or Firm*—William T. Han; Ratner & Prestia; William T. King

[57] ABSTRACT

HLIG-1 polypeptides and polynucleotides and methods for producing such polypeptides by recombinant techniques are disclosed. Also disclosed are methods for utilizing HLIG-1 polypeptides and polynucleotides in the design of protocols for the treatment of neurological disorders such as Alzheimer's disease, multiple sclerosis and abnormal neural development; endocrine disorders such as diabetes; and heart disease, among others and diagnostic assays for such conditions.

16 Claims, No Drawings

```
                               SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 4843 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

GCTTCGCGGC GCGTTCCAGA CAAGATGGCG CGGCCGGTCC GGGGAGGGCT CGGGGCCCCG      60

CGCCGCTCGC CTTGCCTTCT CCTTCTCTGG CTGCTTTTGC TTCGGCTGGA GCCGGTGACC     120

GCCGCGGCCG GCCCGCGGGC GCCCTGCGCG GCCGCCTGCA CTTGCGCTGG GGACCCCTGC     180

ACTTGCGCTG GGGACTCGCT GGACTGCGGT GGGCGCGGGC TGGCTGCGTT GCCCGGGGAC     240

CTGCCCTCCT GGACGCGGAG CCTAAACCTG AGTTACAACA AACTCGCTGA GATTGACCCT     300

GCTGGTTTTG AGGACTTGCC GAACCTACAG GAAGTGTACC TCAATAATCA TGAGTTGACA     360

GCGGTAGCAT CACTGGGCGC TGGTTCATCA CAAGTAGTCG CTCTCTTTCT GCAGCAGCAA     420

CAGAATCGCA GCCTCGACGG GAGCCAGCTG AAGGCCTACC TCTCCCTAGA AGTGTTAGAT     480

CTGAATCTGA ACAACATCAC GGAAGTGCGG AACACCTACT TTCCACACGG ACCGCCTATA     540

AAGGAGCTCA ACCTGGCAGG CAATCGGATT GGCACCCTGG AGTTGGGAGC ATTTGATGGT     600

CTGTCACGGT CGCTGCTAAC TCTTCGCCTG AGCAAAAACA GGATCACCCA GCTTCCTGTA     660

AGAGCATTCA AGCTACCCAG GCTGACACAA CTGGACCTCA ATCGGAACAG GATTCGGCTG     720

ATAGAGGGCC TCACCTTCCA GGGGCTCAAC AGCTTGGAGG TGCTGAAGCT TCAGCGAAAC     780

AACATCAGCA AACTGACAGA TGGGGCCTTC TGGGGACTGT CCAAAATGCA TGTGCTGCAC     840

CTGGAGTACG ACAGCCTGGT AGAAGTGAAC AGCGGCTCGC TCTACGGCCT CACGGCCCTG     900

CATCAGCTCC ACCTCAGCAA CAATTCCATC GCTCGCATTC ACCGCAAGGG CTGGAGCTTC     960

TGCCAGAAGC TGCATGAGTT GGTCCTGTCC TTCAACAACC TGACACGGCT GGACGAGGAG    1020

AGCCTGGCCG AGCTGAGCAG CCTGAGTGTC CTGCGTCTCA GCCACAATTC CATCAGCCAC    1080

ATTGCGGAGG GTGCCTTCAA GGGACTCAGG AGCCTGCGAG TCTTGGATCT GGACCATAAC    1140

GAGATTTCGG GCACAATAGA GGACACGAGC GGCGCCTTCT CAGGGCTCGA ATTCGGCCAC    1200

AGCAAGCTGA CTCTGTTTGG AAACAAGATC AAGTCTGTGG CTAAGAGAGC ATTCTCGGGG    1260

CTGGAAGGCC TGGAGCACCT GAACCTTGGA GGGAATGCGA TCAGATCTGT CCAGTTTGAT    1320

GCCTTTGTGA AGATGAAGAA TCTTAAAGAG CTCCATATCA GCAGCGACAG CTTCCTGTGT    1380

GACTGCCAGC TGAAGTGGCT GCCCCCGTGG CTAATTGGCA GGATGCTGCA GGCCTTTGTG    1440

ACAGCCACCT GTGCCCACCC AGAATCACTG AAGGGTCAGA GCATTTTCTC TGTGCCACCA    1500

GAGAGTTTCG TGTGCGATGA CTTCCTGAAG CCACAGATCA TCACCCAGCC AGAAACCACC    1560

ATGGCTATGG TGGGCAAGGA CATCCGGTTT ACATGCTCAG CAGCCAGCAG CAGCAGCTCC    1620
```

-continued

```
CCCATGACCT TTGCCTGGAA GAAAGACAAT GAAGTCCTGA CCAATGCAGA CATGGAGAAC    1680

TTTGTCCACG TCCACGCGCA GGACGGGAA GTGATGGAGT ACACCACCAT CCTGCACCTC     1740

CGTCAGGTCA CTTTCGGGCA CGAGGGCCGC TACCAATGTG TCATCACCAA CCACTTTGGC    1800

TCCACCTATT CACATAAGGC CAGGCTCACC GTGAATGTGT TGCCATCATT CACCAAAACG    1860

CCCCACGACA TAACCATCCG GACCACCACC GTGGCCCGCC TCGAATGTGC TGCCACAGGT    1920

CACCCAAACC CTCAGATTGC CTGGCAGAAG GATGGAGGCA CGGATTTCCC CGCTGCCCGT    1980

GAGCGACGCA TGCATGTCAT GCCGGATGAC GACGTGTTTT TCATCACTGA TGTGAAAATA    2040

GATGACGCAG GGGTTTACAG CTGTACTGCT CAGAACTCAG CCGGTTCTAT TTCAGCTAAT    2100

GCCACCCTGA CTGTCCTAGA GACCCCATCC TTGGTGGTCC CCTTGGAAGA CCGTGTGGTA    2160

TCTGTGGGAG AAACAGTGGC CCTCCAATGC AAAGCCACGG GGAACCCTCC GCCCCGCATC    2220

ACCTGGTTCA AGGGGACCG CCCGCTGAGC CTCACTGAGC GGCACCACCT GACCCCTGAC     2280

AACCAGCTCC TGGTGGTTCA GAACGTGGTG GCAGAGGATG CGGGCCGATA TACCTGTGAG    2340

ATGTCCAACA CCCTGGGCAC GGAGCGAGCT CACAGCCAGC TGAGCGTCCT GCCCGCAGCA    2400

GGCTGCAGGA AGGATGGGAC CACGGTAGGC ATCTTCACCA TTGCTGTCGT GAGCAGCATC    2460

GTCCTGACGT CACTGGTCTG GGTGTGCATC ATCTACCAGA CCAGGAAGAA GAGTGAAGAG    2520

TACAGTGTCA CCAACACAGA TGAAACCGTC GTGCCACCAG ATGTTCCAAG CTACCTCTCT    2580

TCTCAGGGGA CCCTTTCTGA CCGACAAGAA ACCGTGGTCA GGACCGAGGG TGGCCCTCAG    2640

GCCAATGGGC ACATTGAGAG CAATGGTGTG TGTCCAAGAG ATGCAAGCCA CTTTCCAGAG    2700

CCCGACACTC ACAGCGTTGC CTGCAGGCAG CCAAAGCTCT GTGCTGGGTC TGCGTATCAC    2760

AAAGAGCCGT GGAAAGCGAT GGAGAAAGCT GAAGGGACAC CTGGGCCACA TAAGATGGAA    2820

CACGGTGGCC GGGTCGTATG CAGTGACTGC AACACCGAAG TGGACTGTTA CTCCAGGGGA    2880

CAAGCCTTCC ACCCCCAGCC TGTGTCCAGA GACAGCGCAC AGCCAAGTGC GCCAAATGGC    2940

CCGGAGCCGG GTGGGAGTGA CCAAGAGCAT TCTCCACATC ACCAGTGCAG CAGGACTGCC    3000

GCTGGGTCCT GCCCCGAGTG CCAAGGGTCG CTCTACCCCA GTAACCACGA TAGAATGCTG    3060

ACGGCTGTGA AGAAAAAGCC AATGGCATCT CTAGATGGGA AGGGGATTC TTCCTGGACT     3120

TTAGCAAGGT TGTATCACCC GGACTCCACA GAGCTACAGC CTGCATCTTC ATTAACTTCA    3180

GGCAGTCCAG AGCGCGCGGA AGCCCAGTAC TTGCTTGTTT CCAATGGCCA CCTCCCCAAA    3240

GCATGTGACG CCAGTCCCGA GTCCACGCCA CTGACAGGAC AGCTCCCCGG GAAACAGAGG    3300

GTGCCACTGC TGTTGGCACC AAAAAGCTAG GTTTTGTCTA CCTCAGTTCT TGTCATACCA    3360

ATCTCTACGG GAAAGAGAGG TAGGAGAGGC TGCGAGGAAG CTTGGGTTCA AGCGTCACTC    3420

ATCTGTACAT AGTTGTAACT CCCATGTGGA GTATCAGTCG CTCACAGGAC TTGGATCTGA    3480

AGCACAGTAA ACGCAAGAGG GGATTTGTGT ACAAAAGGCA AAAAAGTAT TTGATATCAT     3540

TGTACATAAG AGTTTTCAGA GATTTCATAT ATATCTTTTA CAGAGGCTAT TTTAATCTTT    3600

AGTGCATGGT TAACAGAAAA AAATTATACA ATTTTGACAA TATTATTTTT CGTATCAGGT    3660

TGCTGTTTAA TTTTGGAGGG GGTGGGGAAA TAGTTCTGGT GCCTTAACGC ATGGCTGGAA    3720

TTTATAGAGG CTACAACCAC ATTTGTTCAC AGGAGTTTTT GGTGCGGGGT GGGAAGGATG    3780

GAAGGCCTTG GATTTATATT GCACTTCATA GACCCCTAGG CTGCTGTGCG GTGGGACTCC    3840

ACATGCGCCG GAAGGAGCTT CAGGTGAGCA CTGCTCATGT GTGGATGCCC CTGCAACAGG    3900

CTTCCCTGTC TGTAGAGCCA GGGGTGCAAG TGCCATCCAC ACTTGCAGTG AATGGCTTTT    3960

CCTTTTAGGT TTAAGTCCTG TCTGTCTGTA AGGCGTAGAA TCTGTCCGTC TGTAAGGCGT    4020
```

```
AGAATGAGGG TTGTTAATCC ATCACAAGCA AAAGGTCAGA ACAGTTAAAC ACTGCCTTTC     4080

CTCCTCCTCT TATTTTATGA TAAAAGCAAA TGTGGCCTTC TCAGTATCAT TCGATTGCTA     4140

TTTGAGACTT TTAAATTAAG GTAAAGGCTG CTGGTGTTGG TACCTGTGGA TTTTTCTATA     4200

CTGATGTTTT CGTTTTGCCA ATATAATGAG TATTACATTG GCCTTGGGGG ACAGAAAGGA     4260

GGAAGTTCTG ACTTTTCAGG GCTACCTTAT TTCTACTAAG GACCCAGAGC AGGCCTGTCC     4320

ATGCCATTCC TTCGCACAAG ATGAAACTGA GCTGGGACTG GAAAGGACAG CCCTTGACCT     4380

GGGTTTCTGG GTATAATTTG CACTTTTGAG ACTGGTAGCT AACCATCTTA TGAGTGCCAA     4440

TGTGTCATTT AGTAAAACTT AAATAGAAAC AAGGTCCTTC AAATGTTCCT TTGGCCAAAA     4500

GCTGAAGGGA GTTACTGAGA AAATAGTTAA CAATTACTGT CAGGTGTCAT CACTGTTCAA     4560

AAGGTAAGCA CATTTAGAAT TTTGTTCTTG ACAGTTAACT GACTAATCTT ACTTCCACAA     4620

AATATGTGAA TTTGCTGCTT CTGAGAGGCA ATGTGAAAGA GGGAGTATTA CTTTTATGTA     4680

CAAAGTTATT TATTTATAGA AATTTTGGTA CAGTGTACAT TGAAAACCAT GTAAAATATT     4740

GAAGTGTCTA ACAATGGCA TTGAAGTGTC TTTAATAAAG GTTCATTTAT AAAAGTCAAA      4800

AAAAAAAAAA AAAAAAAAAA AAAAAAAAAA AAAAAAAAAA AAA                       4843

(2) INFORMATION FOR SEQ ID NO:2:

(i) SEQUENCE CHARACTERISTICS:
        (A) LENGTH: 1101 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Ala Arg Pro Val Arg Gly Gly Leu Gly Ala Pro Arg Arg Ser Pro
 1               5                  10                  15

Cys Leu Leu Leu Leu Trp Leu Leu Leu Arg Leu Glu Pro Val Thr
                20                  25                  30

Ala Ala Ala Gly Pro Arg Ala Pro Cys Ala Ala Ala Cys Thr Cys Ala
            35                  40                  45

Gly Asp Pro Cys Thr Cys Ala Gly Asp Ser Leu Asp Cys Gly Gly Arg
    50                  55                  60

Gly Leu Ala Ala Leu Pro Gly Asp Leu Pro Ser Trp Thr Arg Ser Leu
65                  70                  75                  80

Asn Leu Ser Tyr Asn Lys Leu Ala Glu Ile Asp Pro Ala Gly Phe Glu
                85                  90                  95

Asp Leu Pro Asn Leu Gln Glu Val Tyr Leu Asn Asn His Glu Leu Thr
            100                 105                 110

Ala Val Ala Ser Leu Gly Ala Gly Ser Ser Gln Val Val Ala Leu Phe
        115                 120                 125

Leu Gln Gln Gln Asn Arg Ser Leu Asp Gly Ser Gln Leu Lys Ala
    130                 135                 140

Tyr Leu Ser Leu Glu Val Leu Asp Leu Asn Leu Asn Asn Ile Thr Glu
145                 150                 155                 160

Val Arg Asn Thr Tyr Phe Pro His Gly Pro Pro Ile Lys Glu Leu Asn
                165                 170                 175

Leu Ala Gly Asn Arg Ile Gly Thr Leu Glu Leu Gly Ala Phe Asp Gly
            180                 185                 190

Leu Ser Arg Ser Leu Leu Thr Leu Arg Leu Ser Lys Asn Arg Ile Thr
```

-continued

```
            195                 200                 205
Gln Leu Pro Val Arg Ala Phe Lys Leu Pro Arg Leu Thr Gln Leu Asp
            210                 215                 220
Leu Asn Arg Asn Arg Ile Arg Leu Ile Glu Gly Leu Thr Phe Gln Gly
225                 230                 235                 240
Leu Asn Ser Leu Glu Val Leu Lys Leu Gln Arg Asn Asn Ile Ser Lys
                245                 250                 255
Leu Thr Asp Gly Ala Phe Trp Gly Leu Ser Lys Met His Val Leu His
            260                 265                 270
Leu Glu Tyr Asp Ser Leu Val Glu Val Asn Ser Gly Ser Leu Tyr Gly
                275                 280                 285
Leu Thr Ala Leu His Gln Leu His Leu Ser Asn Asn Ser Ile Ala Arg
            290                 295                 300
Ile His Arg Lys Gly Trp Ser Phe Cys Gln Lys Leu His Glu Leu Val
305                 310                 315                 320
Leu Ser Phe Asn Asn Leu Thr Arg Leu Asp Glu Ser Leu Ala Glu
                325                 330                 335
Leu Ser Ser Leu Ser Val Leu Arg Leu Ser His Asn Ser Ile Ser His
            340                 345                 350
Ile Ala Glu Gly Ala Phe Lys Gly Leu Arg Ser Leu Arg Val Leu Asp
            355                 360                 365
Leu Asp His Asn Glu Ile Ser Gly Thr Ile Glu Asp Thr Ser Gly Ala
            370                 375                 380
Phe Ser Gly Leu Glu Phe Gly His Ser Lys Leu Thr Leu Phe Gly Asn
385                 390                 395                 400
Lys Ile Lys Ser Val Ala Lys Arg Ala Phe Ser Gly Leu Glu Gly Leu
                405                 410                 415
Glu His Leu Asn Leu Gly Gly Asn Ala Ile Arg Ser Val Gln Phe Asp
                420                 425                 430
Ala Phe Val Lys Met Lys Asn Leu Lys Glu Leu His Ile Ser Ser Asp
            435                 440                 445
Ser Phe Leu Cys Asp Cys Gln Leu Lys Trp Leu Pro Pro Trp Leu Ile
            450                 455                 460
Gly Arg Met Leu Gln Ala Phe Val Thr Ala Thr Cys Ala His Pro Glu
465                 470                 475                 480
Ser Leu Lys Gly Gln Ser Ile Phe Ser Val Pro Pro Glu Ser Phe Val
                485                 490                 495
Cys Asp Asp Phe Leu Lys Pro Gln Ile Ile Thr Gln Pro Glu Thr Thr
            500                 505                 510
Met Ala Met Val Gly Lys Asp Ile Arg Phe Thr Cys Ser Ala Ala Ser
            515                 520                 525
Ser Ser Ser Ser Pro Met Thr Phe Ala Trp Lys Lys Asp Asn Glu Val
530                 535                 540
Leu Thr Asn Ala Asp Met Glu Asn Phe Val His Val His Ala Gln Asp
545                 550                 555                 560
Gly Glu Val Met Glu Tyr Thr Thr Ile Leu His Leu Arg Gln Val Thr
                565                 570                 575
Phe Gly His Glu Gly Arg Tyr Gln Cys Val Ile Thr Asn His Phe Gly
            580                 585                 590
Ser Thr Tyr Ser His Lys Ala Arg Leu Thr Val Asn Val Leu Pro Ser
                595                 600                 605
Phe Thr Lys Thr Pro His Asp Ile Thr Ile Arg Thr Thr Thr Val Ala
            610                 615                 620
```

```
Arg Leu Glu Cys Ala Ala Thr Gly His Pro Asn Pro Gln Ile Ala Trp
625                 630                 635                 640

Gln Lys Asp Gly Gly Thr Asp Phe Pro Ala Ala Arg Glu Arg Arg Met
            645                 650                 655

His Val Met Pro Asp Asp Val Phe Phe Ile Thr Asp Val Lys Ile
            660                 665                 670

Asp Asp Ala Gly Val Tyr Ser Cys Thr Ala Gln Asn Ser Ala Gly Ser
            675                 680                 685

Ile Ser Ala Asn Ala Thr Leu Thr Val Leu Glu Thr Pro Ser Leu Val
            690                 695                 700

Val Pro Leu Glu Asp Arg Val Val Ser Val Gly Glu Thr Val Ala Leu
705                 710                 715                 720

Gln Cys Lys Ala Thr Gly Asn Pro Pro Arg Ile Thr Trp Phe Lys
                725                 730                 735

Gly Asp Arg Pro Leu Ser Leu Thr Glu Arg His His Leu Thr Pro Asp
            740                 745                 750

Asn Gln Leu Leu Val Val Gln Asn Val Val Ala Glu Asp Ala Gly Arg
        755                 760                 765

Tyr Thr Cys Glu Met Ser Asn Thr Leu Gly Thr Glu Arg Ala His Ser
770                 775                 780

Gln Leu Ser Val Leu Pro Ala Ala Gly Cys Arg Lys Asp Gly Thr Thr
785                 790                 795                 800

Val Gly Ile Phe Thr Ile Ala Val Ser Ser Ile Val Leu Thr Ser
            805                 810                 815

Leu Val Trp Val Cys Ile Ile Tyr Gln Thr Arg Lys Lys Ser Glu Glu
            820                 825                 830

Tyr Ser Val Thr Asn Thr Asp Glu Thr Val Val Pro Pro Asp Val Pro
            835                 840                 845

Ser Tyr Leu Ser Ser Gln Gly Thr Leu Ser Asp Arg Gln Glu Thr Val
    850                 855                 860

Val Arg Thr Glu Gly Gly Pro Gln Ala Asn Gly His Ile Glu Ser Asn
865                 870                 875                 880

Gly Val Cys Pro Arg Asp Ala Ser His Phe Pro Glu Pro Asp Thr His
                885                 890                 895

Ser Val Ala Cys Arg Gln Pro Lys Leu Cys Ala Gly Ser Ala Tyr His
            900                 905                 910

Lys Glu Pro Trp Lys Ala Met Glu Lys Ala Glu Gly Thr Pro Gly Pro
            915                 920                 925

His Lys Met Glu His Gly Gly Arg Val Val Cys Ser Asp Cys Asn Thr
    930                 935                 940

Glu Val Asp Cys Tyr Ser Arg Gly Gln Ala Phe His Pro Gln Pro Val
945                 950                 955                 960

Ser Arg Asp Ser Ala Gln Pro Ser Ala Pro Asn Gly Pro Glu Pro Gly
                965                 970                 975

Gly Ser Asp Gln Glu His Ser Pro His His Gln Cys Ser Arg Thr Ala
            980                 985                 990

Ala Gly Ser Cys Pro Glu Cys Gln Gly Ser Leu Tyr Pro Ser Asn His
            995                 1000                1005

Asp Arg Met Leu Thr Ala Val Lys Lys Lys Pro Met Ala Ser Leu Asp
    1010                1015                1020

Gly Lys Gly Asp Ser Ser Trp Thr Leu Ala Arg Leu Tyr His Pro Asp
025                 1030                1035                1040
```

```
Ser Thr Glu Leu Gln Pro Ala Ser Ser Leu Thr Ser Gly Ser Pro Glu
            1045                1050                1055

Arg Ala Glu Ala Gln Tyr Leu Leu Val Ser Asn Gly His Leu Pro Lys
        1060                1065                1070

Ala Cys Asp Ala Ser Pro Glu Ser Thr Pro Leu Thr Gly Gln Leu Pro
    1075                1080                1085

Gly Lys Gln Arg Val Pro Leu Leu Leu Ala Pro Lys Ser
  1090                1095                1100
```

(2) INFORMATION FOR SEQ ID NO:3:

(i) SEQUENCE CHARACTERISTICS:
        (A) LENGTH: 3159 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
ACGCCCCACG ACATAACCAT CCGGACCACC ACCGTGGCCC GCCTCGAATG TGCTGCCACA      60

GGTCACCCAA ACCCTCAGAT TGCCTGGCAG AAGGATGGAG GCACGGATTT CCCCGCTGCC     120

CGTGAGCGAC GCATGCATGT CATGCCGGAT GACGACGTGT TTTTCATCAC TGATGTGAAA     180

ATAGATGACG CAGGGGTTTA CAGCTGTACT GCTCAGAACT CAGCCGGTTC TATTGNTACA     240

GCTAATGCCA CCCTGACTGT CCTAGAGACC CCATCCTTGG TGGTCCCCTT GGAAGACCGT     300

GTGGTATCTG TGGGAGAAAC AGTGGCCCTC AATGCAAAG CCACGGGGAA CCCTCTGCCC      360

CGCATCACCT GGTTCAAGGG GGACCTCCCG CTGAAGACCT GCACTGAGCC GGGCACCACT     420

TGACCCCTGA CAACCAGCTC CTGGTGGTTC AGAACGTGGT GGGCAGAGGA TGCGGGCCGA     480

TATACCTGTG AGATGTCCAA CACCCTGGGC ACGGAGCGAG CTCACAGTCC AGCTGAGCGT     540

CCCTGCCCGC AGACAGGCTG CAGGTAAGGA TTGGAACCAC GGTTGGCATC TTCCACCATT     600

GACTGTCGTG AGCCAGCATC GTCCTGACGT CACTGGATCT TGGGTTTGGA TTCATCTATC     660

AGAACCAGGA AGAAGAGTGA AGAGTTACAG TTTTCCCCAC AACCAGGTTG AAAACCGTTG     720

GTGGCACCAG ATGTTCCAAG CTACCTCTCT TCTCAGGGGA CCCTTTCTGA CCGACAAGAA     780

ACCGTGGTCC AGGACCGAGG GTTCGGCCCT GAGGGCAATG GGCACATTGA GAGCAATGGT     840

GTGTGTCCAA GAGATGCAAG CCACTTTCCA GAGCCCGACA CTCACAGCGT TGCCTGCAGG     900

CAGCCAAAGC TCTGTGCTGG GTCTGGGTAT CACAAAGAGC CGTGGAAAGC GATGGAGAAA     960

GCTGGAAGGG ACACCTGGGC ACATGAAGA TGGAACACG GTGGACCGGG TCGTATGCAG     1020

TGACTGCAAC ACCGAAGTGG CAGAGACTGT TTACTCCAGG GGAACAAGCC TTCCACCCCC    1080

AGCCTGTGTC CAGAGGACAG TGCACAGCCA AGTGGGCCAA AATGGTCCCG GAGCCGGGTG    1140

GGGAAGTGAC CAAGAGGCAT TCTTCCACAT CACCATTGCA GGAGGATTGC CGTTGGGTCC    1200

TGCCCCGAGT GGCCCAGGGT TGTTTTTAAC CCCATTAACC ACGTTAGAAT GTTTTTTGAC    1260

GGTTTTTGAA GGAAAAGCCA TTGGCATCTC TAGATGGGAA AGGGGATTCT TCCTGGACTT    1320

TAGCAAGGTT GTATCACCCG GACTCCACAG AGCTACAGCC TGCATCTTCA TTAACTTCAG    1380

GCAGTCCAGA GCGCGCGGAA GCCCAGTACT TGCTTGTTTC CAATGGCCAC CTCCCCAAAG    1440

CATGTGACGC CAGTCCCGAG TCCACGCCAC TGACAGGACA GCTCCCCGGG AAACAGAGGG    1500

TGCCACTGCT GTTGGCACCA AAAGCTAGG TTTTGTCTAC CTCAGTTCTT GGTCATACCA     1560

ATCTCTACGG GAAAGAGAGG TAGGAGAGGC TGCGAGGAAG CTTGGGTTCA AGCGTCACTC    1620
```

-continued

```
ATCTGTACAT AGTTGTAACT CCCATGTGGA GTATCCAGTC GTTCACAGGA CTTGGGATCT    1680

GAAGCACAGT AAACGCAAGA GGGGGATTTG TGTACCAAAA GGCAAAAAAA AGTATTTGAT    1740

ATCCATTGTA CCATAAGGGT TTTCAGGGGT TCATATATA TCCTTTTAAC AGAGGTTATT    1800

TTAATCTTTA GTGCATGGTT AACCGGAAAA AATTTTTCCA TTTTGGCCAT TTTATTTTTC    1860

CGTATCCAGG TTGCTGTTTA ATTTTGGAGG GGGTTGGGGA AATAGTTCTG GTGCCTTAAC    1920

GCATGGCTGG GAATTTATAG AGGCTACAAC CACATTTGTT CACAGGAAGT TTTTGGTGCG    1980

GGGTGGGAAG GATGGAAGGC CTTGGAATTT ATATTGCACT TCATAGACCC CTAGGCTGCT    2040

GTGCGGTGGG ACTCCACATG CGCCCGGAAG GAGCTTTCAG GTGAGCACTG CTCATGTGTG    2100

GATGCCCCTG CAACAGGCTT CCCTGTCTGT AGAGCCAGGG GTGCAAGTGC CCATCCACAC    2160

TTGCAGTGAA TGGCTTTTCC TTTTAGTTTT AAGTCCTGTC TGTTTTTAAG GCGTAGGATT    2220

TGTCCTTCTG TAAGGCGTGG AATGAGGGTT GTTAATCCAT CACAAGCAAA AGGTCCGAAC    2280

CGTTAAACAC TGCCTTTCCT CCTCCTTATT TTGGTTCCCT TATTTTATGT TAAAAGCAAA    2340

TGTGGCCTTC TCAGTATCAT TCGATTGCTA TTTGAGACTT TTAAATTAAG GTAAAGGCTG    2400

CTGGTGTTGG TACCTGTGGA TTTTTCTATA CTGATGTTTT CGTTTTGCCA ATATAATGAG    2460

TATTACATTG GCCTTGGGGG ACAGAAAGGA GGAAGTTCTG ACTTTTCAGG GCTACCTTAT    2520

TTCTACTAAG GACCCAGAGC AGGCCTGTCC ATGCCATTCC TTCGCACAGA TGAAACTGAG    2580

CTGGGACTGG AAAGGACAGC CCTTGACCTG GGTTCTGGGT ATAATTTGCA CTTTTGAGAC    2640

TGGTAGCTAA CCATCTTATG AGTGCCAATG TGTCATTTAG TAAAACTTAA ATAGAAACAA    2700

GGTCCTTCAA ATGTTCCTTT GGCCAAAAGC TGAAGGGAGT TACTGAGAAA ATAGTTAACA    2760

ATTACTGTCA GGTGTCATCA CTGTTCAAAA GGTAAGCACA TTTAGAATTT TGTTCTTGAC    2820

AGTTAACTGA CTAATCTTAC TTCCACAAAA TATGTGAATT TGCTGCTTCT GAGAGGCAAT    2880

GTGAAGAGG GAGTATTACT TTTATGTACA AAGTTATTTA TTTATAGAAA TTTTGGTACA    2940

GTGTACATTG AAAACCATGT AAAATATTGA AGTGTCTAAC AAATGGCATT GAAGTGTCTT    3000

TAATAAAGGT TCATTTATAA ATGTCAAAAT AANNNNAAGT TATTTATTTA TAGAAATTTT    3060

GGTACAGTGT ACATTGAAAA CCATGTAAAA TATTGAAGTG TNCTAACAAA TGGCATTGAA    3120

GTGTNCTTTA ATAAAGGTTC ATTTATAAAT GTCNNAAAA                           3159
```

(2) INFORMATION FOR SEQ ID NO:4:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Thr Pro His Asp Ile Thr Ile Arg Thr Thr Val Ala Arg Leu Glu
 1               5                  10                  15

Cys Ala Ala Thr Gly His Pro Asn Pro Gln Ile Ala Trp Gln Lys Asp
                20                  25                  30

Gly Gly Thr Asp Phe Pro Ala Ala Arg Glu Arg Arg Met His Val Met
            35                  40                  45

Pro Asp Asp Asp Val Phe Phe Ile Thr Asp Val Lys Ile Asp Asp Ala
        50                  55                  60

Gly Val Tyr Ser Cys Thr Ala Gln Asn Ser Ala Gly Ser Ile Xaa Thr
65                  70                  75                  80
```

```
Ala Asn Ala Thr Leu Thr Val Leu Glu Thr Pro Ser Leu Val Val Pro
                 85                  90                  95

Leu Glu Asp Arg Val Val Ser Val Gly Glu Thr Val Ala Leu Gln Cys
            100                 105                 110

Lys Ala Thr Gly Asn Pro Leu Pro Arg Ile Thr Trp Phe Lys Gly Asp
        115                 120                 125

Leu Pro Leu Lys Thr Cys Thr Glu Pro Gly Thr Thr
    130                 135                 140

(2) INFORMATION FOR SEQ ID NO:5:

(i) SEQUENCE CHARACTERISTICS:
        (A) LENGTH: 1091 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Met Ala Arg Pro Gly Pro Gly Val Leu Gly Ala Pro Arg Leu Ala Pro
 1               5                  10                  15

Arg Leu Leu Leu Trp Leu Leu Leu Leu Leu Gln Trp Pro Glu Ser
             20                  25                  30

Ala Gly Ala Gln Ala Arg Pro Arg Ala Pro Cys Ala Ala Cys Thr
         35                  40                  45

Cys Ala Gly Asn Ser Leu Asp Cys Ser Gly Arg Gly Leu Ala Thr Leu
    50                  55                  60

Pro Arg Asp Leu Pro Ser Trp Thr Arg Ser Leu Asn Leu Ser Tyr Asn
65                  70                  75                  80

Arg Leu Ser Glu Ile Asp Ser Ala Ala Phe Glu Asp Leu Thr Asn Leu
                85                  90                  95

Gln Glu Val Tyr Leu Asn Ser Asn Glu Leu Thr Ala Ile Pro Ser Leu
            100                 105                 110

Gly Thr Ala Ser Ile Gly Val Val Ser Leu Phe Leu Gln His Asn Lys
        115                 120                 125

Ile Leu Ser Val Asp Gly Ser Gln Leu Lys Ser Tyr Leu Ser Leu Glu
    130                 135                 140

Val Leu Asp Leu Ser Ser Asn Asn Ile Thr Glu Ile Arg Ser Ser Cys
145                 150                 155                 160

Phe Pro Asn Gly Leu Arg Ile Arg Glu Leu Asn Leu Ala Ser Asn Arg
                165                 170                 175

Ile Ser Ile Leu Glu Ser Gly Ala Phe Asp Gly Leu Ser Arg Ser Leu
            180                 185                 190

Leu Thr Leu Arg Leu Ser Lys Asn Arg Ile Thr Gln Leu Pro Val Lys
        195                 200                 205

Ala Phe Lys Leu Pro Arg Leu Thr Gln Leu Asp Leu Asn Arg Asn Arg
    210                 215                 220

Ile Arg Leu Ile Glu Gly Leu Thr Phe Gln Gly Leu Asp Ser Leu Glu
225                 230                 235                 240

Val Leu Arg Leu Gln Arg Asn Asn Ile Ser Arg Leu Thr Asp Gly Ala
                245                 250                 255

Phe Trp Gly Leu Ser Lys Met His Val Leu His Leu Glu Tyr Asn Ser
            260                 265                 270

Leu Val Glu Val Asn Ser Gly Ser Leu Tyr Gly Leu Thr Ala Leu His
        275                 280                 285
```

-continued

```
Gln Leu His Leu Ser Asn Asn Ser Ile Ser Arg Ile Gln Arg Asp Gly
    290                 295                 300

Trp Ser Phe Cys Gln Lys Leu His Glu Leu Ile Leu Ser Phe Asn Asn
305                 310                 315                 320

Leu Thr Arg Leu Asp Glu Glu Ser Leu Ala Glu Leu Ser Ser Leu Ser
                325                 330                 335

Ile Leu Arg Leu Ser His Asn Ala Ile Ser His Ile Ala Glu Gly Ala
                340                 345                 350

Phe Lys Gly Leu Lys Ser Leu Arg Val Leu Asp Leu Asp His Asn Glu
            355                 360                 365

Ile Ser Gly Thr Ile Glu Asp Thr Ser Gly Ala Phe Thr Gly Leu Asp
370                 375                 380

Asn Leu Ser Lys Leu Thr Leu Phe Gly Asn Lys Ile Lys Ser Val Ala
385                 390                 395                 400

Lys Arg Ala Phe Ser Gly Leu Glu Ser Leu Glu His Leu Asn Leu Gly
                405                 410                 415

Glu Asn Ala Ile Arg Ser Val Gln Phe Asp Ala Phe Ala Lys Met Lys
                420                 425                 430

Asn Leu Lys Glu Leu Tyr Ile Ser Ser Glu Ser Phe Leu Cys Asp Cys
            435                 440                 445

Gln Leu Lys Trp Leu Pro Pro Trp Leu Met Gly Arg Met Leu Gln Ala
    450                 455                 460

Phe Val Thr Ala Thr Cys Ala His Pro Glu Ser Leu Lys Gly Gln Ser
465                 470                 475                 480

Ile Phe Ser Val Leu Pro Asp Ser Phe Val Cys Asp Asp Phe Pro Lys
                485                 490                 495

Pro Gln Ile Ile Thr Gln Pro Glu Thr Thr Met Ala Val Val Gly Lys
                500                 505                 510

Asp Ile Arg Phe Thr Cys Ser Ala Ser Ser Ser Ser Ser Pro Met
            515                 520                 525

Thr Phe Ala Trp Lys Lys Asp Asn Glu Val Leu Ala Asn Ala Asp Met
    530                 535                 540

Glu Asn Phe Ala His Val Arg Ala Gln Asp Gly Glu Val Met Glu Tyr
545                 550                 555                 560

Thr Thr Ile Leu His Leu Arg His Val Thr Phe Gly His Glu Gly Arg
                565                 570                 575

Tyr Gln Cys Ile Ile Thr Asn His Phe Gly Ser Thr Tyr Ser His Lys
                580                 585                 590

Ala Arg Leu Thr Val Asn Val Leu Pro Ser Phe Thr Lys Ile Pro His
            595                 600                 605

Asp Ile Ala Ile Arg Thr Gly Thr Thr Ala Arg Leu Glu Cys Ala Ala
610                 615                 620

Thr Gly His Pro Asn Pro Gln Ile Ala Trp Gln Lys Asp Gly Gly Thr
625                 630                 635                 640

Asp Phe Pro Ala Ala Arg Glu Arg Arg Met His Val Met Pro Asp Asp
                645                 650                 655

Asp Val Phe Phe Ile Thr Asp Val Lys Ile Asp Asp Met Gly Val Tyr
                660                 665                 670

Ser Cys Thr Ala Gln Asn Ser Ala Gly Ser Val Ser Ala Asn Ala Thr
            675                 680                 685

Leu Thr Val Leu Glu Thr Pro Ser Leu Ala Val Pro Leu Glu Asp Arg
    690                 695                 700
```

-continued

```
Val Val Thr Val Gly Glu Thr Val Ala Phe Gln Cys Lys Ala Thr Gly
705                 710                 715                 720

Ser Pro Thr Pro Arg Ile Thr Trp Leu Lys Gly Gly Arg Pro Leu Ser
            725                 730                 735

Leu Thr Glu Arg His His Phe Thr Pro Gly Asn Gln Leu Leu Val Val
            740                 745                 750

Gln Asn Val Met Ile Asp Asp Ala Gly Arg Tyr Thr Cys Glu Met Ser
            755                 760                 765

Asn Pro Leu Gly Thr Glu Arg Ala His Ser Gln Leu Ser Ile Leu Pro
770                 775                 780

Thr Pro Gly Cys Arg Lys Asp Gly Thr Thr Val Gly Ile Phe Thr Ile
785                 790                 795                 800

Ala Val Val Cys Ser Ile Val Leu Thr Ser Leu Val Trp Val Cys Ile
            805                 810                 815

Ile Tyr Gln Thr Arg Lys Lys Ser Glu Glu Tyr Ser Val Thr Asn Thr
            820                 825                 830

Asp Glu Thr Ile Val Pro Pro Asp Val Pro Ser Tyr Leu Ser Ser Gln
            835                 840                 845

Gly Thr Leu Ser Asp Arg Gln Glu Thr Val Val Arg Thr Glu Gly Gly
            850                 855                 860

His Gln Ala Asn Gly His Ile Glu Ser Asn Gly Val Cys Leu Arg Asp
865                 870                 875                 880

Pro Ser Leu Phe Pro Glu Val Asp Ile His Ser Thr Thr Cys Arg Gln
            885                 890                 895

Pro Lys Leu Cys Val Gly Tyr Thr Arg Glu Pro Trp Lys Val Thr Glu
            900                 905                 910

Lys Ala Asp Arg Thr Ala Ala Pro His Thr Thr Ala His Ser Gly Ser
            915                 920                 925

Ala Val Cys Ser Asp Cys Ser Thr Asp Thr Ala Tyr His Pro Gln Pro
            930                 935                 940

Val Pro Arg Asp Ser Gly Gln Pro Gly Thr Ala Ser Ser Gln Glu Leu
945                 950                 955                 960

Arg Gln His Asp Arg Glu Tyr Ser Pro His His Pro Tyr Ser Gly Thr
            965                 970                 975

Ala Asp Gly Ser His Thr Leu Ser Gly Gly Ser Leu Tyr Pro Ser Asn
            980                 985                 990

His Asp Arg Ile Leu Pro Ser Leu Lys Asn Lys Ala Ala Ser Ala Asp
            995                1000                1005

Gly Asn Gly Asp Ser Ser Trp Thr Leu Ala Lys Leu His Glu Ala Asp
       1010                1015                1020

Cys Ile Asp Leu Lys Pro Ser Pro Thr Leu Ala Ser Gly Ser Pro Glu
025                 1030                1035                1040

Leu Met Glu Asp Ala Ile Ser Thr Glu Ala Gln His Leu Leu Val Ser
                1045                1050                1055

Asn Gly His Leu Pro Lys Ala Cys Asp Ser Ser Pro Glu Ser Val Pro
            1060                1065                1070

Leu Lys Gly Gln Ile Thr Gly Lys Arg Arg Gly Pro Leu Leu Leu Ala
       1075                1080                1085

Pro Arg Ser
      1090
```

(2) INFORMATION FOR SEQ ID NO:6:

(i) SEQUENCE CHARACTERISTICS:

(A) LENGTH: 353 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:6:

Ala Glu Gly Pro Gln Cys Pro Val Ala Cys Thr Cys Ser His Asp Asp
 1               5                  10                  15

Tyr Thr Asp Glu Leu Ser Val Phe Cys Ser Ser Lys Asn Leu Thr His
             20                  25                  30

Leu Pro Asp Asp Ile Pro Val Ser Thr Arg Ala Leu Trp Leu Asp Gly
         35                  40                  45

Asn Asn Leu Ser Ser Ile Pro Ser Ala Ala Phe Gln Asn Leu Ser Ser
 50                  55                  60

Leu Asp Phe Leu Asn Leu Gln Gly Ser Trp Leu Arg Ser Leu Glu Pro
 65                  70                  75                  80

Gln Ala Leu Leu Gly Leu Gln Asn Leu Tyr Tyr Leu His Leu Glu Arg
                 85                  90                  95

Asn Arg Leu Arg Asn Leu Ala Val Gly Leu Phe Thr His Thr Pro Ser
             100                 105                 110

Leu Ala Ser Leu Ser Leu Ser Ser Asn Leu Leu Gly Arg Leu Glu Glu
         115                 120                 125

Gly Leu Phe Gln Gly Leu Ser His Leu Trp Asp Leu Asn Leu Gly Trp
 130                 135                 140

Asn Ser Leu Val Val Leu Pro Asp Thr Val Phe Gln Gly Leu Gly Asn
145                 150                 155                 160

Leu His Glu Leu Val Leu Ala Gly Asn Lys Leu Thr Tyr Leu Gln Pro
                 165                 170                 175

Ala Leu Phe Cys Gly Leu Gly Glu Leu Arg Glu Leu Asp Leu Ser Arg
             180                 185                 190

Asn Ala Leu Arg Ser Val Lys Ala Asn Val Phe Val His Leu Pro Arg
         195                 200                 205

Leu Gln Lys Leu Tyr Leu Asp Arg Asn Leu Ile Thr Ala Val Ala Pro
 210                 215                 220

Gly Ala Phe Leu Gly Met Lys Ala Leu Arg Trp Leu Asp Leu Ser His
225                 230                 235                 240

Asn Arg Val Ala Gly Leu Met Glu Asp Thr Phe Pro Gly Leu Leu Gly
                 245                 250                 255

Leu His Val Leu Arg Leu Ala His Asn Ala Ile Ala Ser Leu Arg Pro
             260                 265                 270

Arg Thr Phe Lys Asp Leu His Phe Leu Glu Glu Leu Gln Leu Gly His
         275                 280                 285

Asn Arg Ile Arg Gln Leu Gly Arg Thr Phe Glu Gly Leu Gly Gln
 290                 295                 300

Leu Glu Val Leu Thr Leu Asn Asp Asn Gln Ile Thr Glu Val Arg Val
305                 310                 315                 320

Gly Ala Phe Ser Gly Leu Phe Asn Val Ala Val Met Asn Leu Ser Gly
                 325                 330                 335

Asn Cys Leu Arg Ser Leu Pro Glu Arg Val Phe Gln Gly Leu Asp Lys
             340                 345                 350

Leu (2) INFORMATION FOR SEQ ID NO:7:

(i) SEQUENCE CHARACTERISTICS:
    (A) LENGTH: 231 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:7:

```
Gly Ile His Ile Pro Gly Gly Val Gly Ile Thr Glu Ala Arg
 1               5                  10                  15

Cys Pro Arg Val Cys Ser Cys Thr Gly Leu Asn Val Asp Cys Ser His
             20                  25                  30

Arg Gly Leu Thr Ser Val Pro Arg Lys Ile Ser Ala Asp Val Glu Arg
             35                  40                  45

Leu Glu Leu Gln Gly Asn Asn Leu Thr Val Ile Tyr Glu Thr Asp Phe
 50                  55                  60

Gln Arg Leu Thr Lys Leu Arg Met Leu Gln Leu Thr Asp Asn Gln Ile
 65                  70                  75                  80

His Thr Ile Glu Arg Asn Ser Phe Gln Asp Leu Val Ser Leu Glu Arg
                 85                  90                  95

Leu Asp Ile Ser Asn Asn Val Ile Thr Thr Val Gly Arg Arg Val Phe
                100                 105                 110

Lys Gly Ala Gln Ser Leu Arg Ser Leu Gln Leu Asp Asn Asn Gln Ile
            115                 120                 125

Thr Cys Leu Asp Glu His Ala Phe Lys Gly Leu Val Glu Leu Glu Ile
130                 135                 140

Leu Thr Leu Asn Asn Asn Asn Leu Thr Ser Leu Pro His Asn Ile Phe
145                 150                 155                 160

Gly Gly Leu Gly Arg Leu Arg Ala Leu Arg Leu Ser Asp Asn Pro Phe
                165                 170                 175

Ala Cys Asp Cys His Leu Ser Trp Leu Ser Arg Phe Leu Arg Ser Ala
            180                 185                 190

Thr Arg Leu Ala Pro Tyr Thr Arg Cys Gln Ser Pro Ser Gln Leu Lys
            195                 200                 205

Gly Gln Asn Val Ala Asp Leu His Asp Gln Glu Phe Lys Cys Ser Gly
210                 215                 220

Leu Thr Glu His Ala Pro Met
225                 230
```

(2) INFORMATION FOR SEQ ID NO:8:

(i) SEQUENCE CHARACTERISTICS:
    (A) LENGTH: 180 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:8:

```
Pro Gly Ala Gly Cys Pro Ser Arg Cys Leu Cys Phe Arg Thr Thr Val
 1               5                  10                  15

Arg Cys Met His Leu Leu Leu Glu Ala Val Pro Ala Val Ala Pro Gln
             20                  25                  30

Thr Ser Ile Leu Asp Leu Arg Phe Asn Arg Ile Arg Glu Ile Gln Pro
             35                  40                  45

Gly Ala Phe Arg Arg Leu Arg Asn Leu Asn Thr Leu Leu Leu Asn Asn
```

-continued

```
                50                      55                      60
Asn Gln Ile Lys Arg Ile Pro Ser Gly Ala Phe Glu Asp Leu Glu Asn
 65              70                  75                      80

Leu Lys Tyr Leu Tyr Leu Tyr Lys Asn Glu Ile Gln Ser Ile Asp Arg
                 85                  90              95

Gln Ala Phe Lys Gly Leu Ala Ser Leu Glu Gln Leu Tyr Leu His Phe
            100             105             110

Asn Gln Ile Glu Thr Leu Asp Pro Asp Ser Phe Gln His Leu Pro Lys
            115             120             125

Leu Glu Arg Leu Phe Leu His Asn Asn Arg Ile Thr His Leu Val Pro
        130             135             140

Gly Thr Phe Asn His Leu Glu Ser Met Lys Arg Leu Arg Leu Asp Ser
145             150             155             160

Asn Thr Leu His Cys Asp Cys Glu Ile Leu Trp Leu Ala Asp Leu Leu
                165             170             175

Lys Thr Tyr Ala
            180
```

HUMAN LIG-1 HOMOLOG (HLIG-1)

This application claims the benefit of U.S. Provisional Application Ser. No. 60/059,448, filed Sep. 22, 1997.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to the immunoglobulin superfamily, hereinafter referred to as HLIG-1. The invention also relates to inhibiting or activating the action of such polynucleotides and polypeptides.

BACKGROUND OF THE INVENTION

The immunoglobulin (Ig) gene superfamily comprises a large number of cell surface glycoproteins that share sequence homology with the V and C domains of antibody heavy and light chains. The Ig superfamily molecules function as receptors for antigen, receptors or counter-receptors for other cell surface molecules including other Ig superfamily molecules and adhesion molecules, and as receptors for cytokines (A. F. Williams et al., Annu. Rev. Immunol. 6:381–405, 1988).

Another protein fold motif of this family is the leucine rich repeat (LRR), which is a segment of 20–29 amino acids with a signature pattern of 4 consensus leucines and an asparagine. LRRs most commonly occur in multiple tandem arrays and have been identified in more than 60 different proteins of diverse function (reviewed in B. Kobe and J. Deisenhofer, Trends-Biochem-Sci. 19, 415–21 (1994) and in B. Kobe and J. Deisenhofer, Curr Op in Struct Biol 5, 409–416 (1995)). Examples of this family are found in a range of organisms and include the insulin binding protein acid labile subunit (ALS), the morphogenic protein "18 wheeler," the neural development protein slit, the receptors for chorionic gonadotropin, lutrophin, and follitrophin, and the transcriptional regulator, CIITA. The crystal structure of one member of this family, porcine ribonuclease inhibitor (RI), has been determined (B. Kobe and J. Deisenhofer, Nature 366, 751–756 (1993)) and serves as a model for the folding of the LRR regions in other proteins. RI consists entirely of 15 LRRs which assume a β-strand-turn-helix-turn conformation and assemble into a toroid shaped horseshoe structure. Although diverse in function and cellular localization, a common property of members of the LRR family is protein interaction which in several instances has been mapped to the unusual structural region of the LRRs. One indication of the nature of this interaction is revealed by the structure of the complex between RI-and its non-native ligand ribonuclease A (B. Kobe and J. Deisenhofer, Nature 374, 183–186 (1995)). As revealed in both the complexed and uncomplexed structure, the conserved residues of the LRR repeat are buried, serving as foundations for the fold. The specificity for differential protein recognition lies in other non-conserved residues in the repeat. A second sequence motif often associated with LRRs is a cysteine cluster containing 4 similarly spaced cysteines and a proline residue. These clusters lie immediately N- or C-terminal, or both, to the tandem LRRs, and most frequently occur in proteins associated with adhesion or receptor function. One example of this subfamily is the insulin binding protein acid labile subunit (ALS) (S R Leong et al., Mol Endocrinol 6, 870–876 (1992)), which forms dimeric complexes with insulin binding proteins (IBP) and trimeric complexes with IBPs and insulin like growth factors (IGFs). These complexes restrict IGFs to the vascular compartment with a long extension of their circulating ½ life, and thereby are critical in the development of endocrine function and in the regulation of glucose homeostasis. A second example is the drosophila protein slit, a secreted protein of glial cells, which is involved in the development of axonal pathways (J M Rothberg et al., Genes Develop. 4, 2169–2187 (1990)).

Recently, LIG-1, a novel mouse membrane glycoprotein, which contains 15 leucine-rich repeats (LRR) and flanking cysteine clusters and 3 Ig-like domains of the C2-type, was identified by Y. Suzuki et al., J. Biol. Chem. 271:22522–22527, (1996). LIG-1 is expressed predominantly in the mouse brain, restricted to a small subset of glial cells such as the Bergmann glial cells and those in the nerve fiber layer of the olfactory bulb. Based on its unique molecular structure and tissue-specific expression, LIG-1 may play a role in neuroglial differentiation, development, and/or maintenance of neural function. This indicates that these receptors have an established, proven history as therapeutic targets. Clearly there is a need for identification and characterization of further receptors which can play a role in preventing, ameliorating or correcting dysfunctions or diseases, including, but not limited to, neurological disorders such as Alzheimer's disease, multiple sclerosis and abnormal neural development; endocrine disorders such as diabetes; and heart disease.

SUMMARY OF THE INVENTION

In one aspect, the invention relates to HLIG-1 polypeptides and recombinant materials and methods for their production. Another aspect of the invention relates to methods for using such HLIG-1 polypeptides and polynucleotides. Such uses include the treatment of neurological disorders such as Alzheimer's disease, multiple sclerosis and abnormal neural development; endocrine disorders such as diabetes; and heart disease, among others. In still another aspect, the invention relates to methods to identify agonists and antagonists using the materials provided by the invention, and treating conditions associated with HLIG-1 imbalance with the identified compounds. Yet another aspect of the invention relates to diagnostic assays for detecting diseases associated with inappropriate HLIG-1 activity or levels.

DESCRIPTION OF THE INVENTION

Definitions

The following definitions are provided to facilitate understanding of certain terms used frequently herein.

"HLIG-1" refers, among others, to a polypeptide comprising the amino acid sequence set forth in SEQ ID NO:2, or an allelic variant thereof.

"Receptor Activity" or "Biological Activity of the Receptor" refers to the metabolic or physiologic function of said HLIG-1 including similar activities or improved activities or these activities with decreased undesirable side-effects. Also included are antigenic and immunogenic activities of said HLIG-1.

"HLIG-1 gene" refers to a polynucleotide comprising the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschul, S. F. et al., *J Molec Biol* (1990) 215:403).

As an illustration, by a polynucleotide having a nucleotide sequence having at least, for example, 95% "identity" to a reference nucleotide sequence of SEQ ID NO:1 is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to HLIG-1 polypeptides (or HLIG-1 proteins). The HLIG-1 polypeptides include the polypeptides of SEQ ID NOS:2 and 4; as well as polypeptides comprising the amino acid sequence of SEQ ID NO:2; and polypeptides comprising the amino acid sequence which have at least 80% identity to that of SEQ ID NO:2 over its entire length, and still more preferably at least 90% identity, and even still more preferably at least 95% identity to SEQ ID NO: 2. Furthermore, those with at least 97–99% are highly preferred. Also included within HLIG-1 polypeptides are polypeptides having the amino acid sequence which have at least 80% identity to the polypeptide having the amino acid sequence of SEQ ID NO: 2 over its entire length, and still more preferably at least 90% identity, and even still more preferably at least 95% identity to SEQ ID NO: 2. Furthermore, those with at least 97–99% are highly preferred. Preferably HLIG-1 polypeptides exhibit at least one biological activity of the receptor.

The HLIG-1 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the HLIG-1 polypeptides are also included in the invention. A fragment is a polypeptide having an amino acid sequence that entirely is the same as part, but not all, of the amino acid sequence of the aforementioned HLIG-1 polypeptides. As with HLIG-1 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 2140, 41–60, 61–80, 81–100, and 101 to the end of HLIG-1 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of HLIG-1 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate receptor activity, including those with a similar activity or an improved activity, or with a decreased undesirable activity. Also included are those that are antigenic or immunogenic in an animal, especially in a human.

Preferably, all of these polypeptide fragments retain the biological activity of the receptor, including antigenic activity. Among the most preferred fragment is that having the amino acid sequence of SEQ ID NO: 4. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The HLIG-1 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to HLIG-1 polynucleotides. HLIG-1 polynucleotides include isolated polynucleotides which encode the HLIG-1 polypeptides and fragments, and polynucleotides closely related thereto. More specifically, HLIG-1 polynucleotide of the invention include a polynucleotide comprising the nucleotide sequence contained in SEQ ID NO:1 encoding a HLIG-1 polypeptide of SEQ ID NO: 2, and polynucleotides having the particular sequences of SEQ ID NOS: 1 and 3. HLIG-1 polynucleotides further include a polynucleotide comprising a nucleotide sequence that has at least 80% identity over its entire length to a nucleotide sequence encoding the HLIG-1 polypeptide of SEQ ID NO:2, and a polynucleotide comprising a nucleotide sequence that is at least 80% identical to that of SEQ ID NO:1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under HLIG-1 polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such HLIG-1 polynucleotides.

HLIG-1 of the invention is structurally related to other proteins of the immunoglobulin superfamily, as shown by the results of sequencing the cDNA encoding human HLIG-1. The cDNA sequence of SEQ ID NO:1 contains an open reading frame (nucleotide number 25 to 3327) encoding a polypeptide of 1101 amino acids of SEQ ID NO:2. The amino acid sequence of Table 1 (SEQ ID NO:2) has about 80.3% identity (using Fasta) in 1101 amino acid residues with mouse LIG-1 (Y. Suzuki et al., J. Biol. Chem. 271:22522–22527, 1996). Furthermore, HLIG-1 is 35.5% identical to rat insulin-like growth factor binding protein over 285 amino acid residues (J. Dai et al., Biochem Biophys. Res. Commun. 188: 304–309, 1992), 30.4% identical to drosophila slit protein over 203 amino acid residues (J. M. Rothberg et al., Genes Dev. 4:2169–2187, 1990) and 32.3% identical to D.melanogaster peroxidasin over 133 amino acid residues (R. E. Nelson et al., EMBO J. 13:3438–3447, 1994). The nucleotide sequence of Table 1 (SEQ ID NO: 1) has about 77.9% identity (using Fasta) in 3577 nucleotide residues with mouse lig-1 gene (Y. Suzuki et al., J. Biol. Chem. 271:22522–22527, 1996). Furthermore, HLIG-1 gene is 86.1% identical to rat CHOT1 gene over 468 nucleotide base residues (W. Mayser et al., FEBS Lett. 305:31–36, 1992). Thus, HLIG-1 polypeptides and polynucleotides of the present invention are expected to have, inter alia, similar biological functions/properties to their homologous polypeptides and polynucleotides, and their utility is obvious to anyone skilled in the art.

TABLE 1[a]

| | |
|---|---|
| 1 | GCTTCGCGGC GCGTTCCAGA CAAGATGGCG CGGCCGGTCC GGGGAGGGCT |
| 51 | CGGGGCCCCG CGCCGCTCGC CTTGCCTTCT CCTTCTCTGG CTGCTTTTGC |
| 101 | TTCGGCTGGA GCCGGTGACC GCCGCGGCCG GCCCGCGGGC GCCCTGCGCG |
| 151 | GCCGCCTGCA CTTGCGCTGG GGACCCCTGC ACTTGCGCTG GGGACTCGCT |
| 201 | GGACTGCGGT GGGCGCGGGC TGGCTGCGTT GCCCGGGGAC CTGCCCTCCT |
| 251 | GGACGCGGAG CCTAAACCTG AGTTACAACA AACTCGCTGA GATTGACCCT |
| 301 | GCTGGTTTTG AGGACTTGCC GAACCTACAG GAAGTGTACC TCAATAATCA |
| 351 | TGAGTTGACA GCGGTAGCAT CACTGGGCGC TGGTTCATCA CAAGTAGTCG |
| 401 | CTCTCTTTCT GCAGCAGCAA CAGAATCGCA GCCTCGACGG GAGCCAGCTG |
| 451 | AAGGCCTACC TCTCCCTAGA AGTGTTAGAT CTGAAACTGA ACAACATCAC |
| 501 | GGAAGTGCGG AACACCTACT TTCCACACGG ACCGCCTATA AAGGAGCTCA |
| 551 | ACCTGGCAGG CAATCGGATT GGCACCCTGG AGTTGGGAGC ATTTGATGGT |
| 601 | CTGTCACGGT CGCTGCTAAC TCTTCGCCTG AGCAAAAACA GGATCACCCA |
| 651 | GCTTCCTGTA AGAGCATTCA AGCTACCCAG GCTGACACAA CTGGACCTCA |
| 701 | ATCGGAACAG GATTCGGCTG ATAGAGGGCC TCACCTTCCA GGGGCTCAAC |
| 751 | AGCTTGGAGG TGCTGAAGCT TCAGCGAAAC AACATCAGCA AACTGACAGA |
| 801 | TGGGGCCTTC TGGGGACTGT CCAAAATGCA TGTGCTGCAC CTGGAGTACG |
| 851 | ACAGCCTGGT AGAAGTGAAC AGCGGCTCGC TCTACGGCCT CACGGCCCTG |
| 901 | CATCAGCTCC ACCTCAGCAA CAATTCCATC GCTCGCATTC ACCGCAAGGG |
| 951 | CTGGAGCTTC TGCCAGAAGC TGCATGAGTT GGTCCTGTCC TTCAACAACC |
| 1001 | TGACACGGCT GGACGAGGAG AGCCTGGCCG AGCTGAGCAG CCTGAGTGTC |
| 1051 | CTGCGTCTCA GCCACAATTC CATCAGCCAG ATTGCGGAGG GTGCCTTCAA |
| 1101 | GGGACTCAGG AGCCTGCGAG TCTTGGATCT GGACCATAAC GAGATTTCGG |
| 1151 | GCACAATAGA GGACACGAGC GGCGCCTTCT CAGGGCTCGA ATTCGGCCAC |
| 1201 | AGCAAGCTGA CTCTGTTTGG AAACAAGATC AAGTCTGTGG CTAAGAGAGC |
| 1251 | ATTCTCGGGG CTGGAAGGCC TGGAGCACCT GAACCTTGGA GGGAATGCGA |

TABLE 1ª-continued

```
1301  TCAGATCTGT CCAGTTTGAT GCCTTTGTGA AGATGAAGAA TCTTAAAGAG
1351  CTCCATATCA GCAGCGACAG CTTCCTGTGT GACTGCCAGC TGAAGTGGCT
1401  GCCCCCGTGG CTAATTGGCA GGATGCTGCA GGCCTTTGTG ACAGCCACCT
1451  GTGCCCACCC AGAATCACTG AAGGGTCAGA GCATTTTCTC TGTGCCACCA
1501  GAGAGTTTCG TGTGCGATGA CTTCCTGAAG CCACAGATCA TCACCCAGCC
1551  AGAAACCACC ATGGCTATGG TGGGCAAGGA CATCCGGTTT ACATGCTCAG
1601  CAGCCAGCAG CAGCAGCTCC CCCATGACCT TTGCCTGGAA GAAAGACAAT
1651  GAAGTCCTGA CCAATGCAGA CATGGAGAAC TTTGTCCACG TCCACGCGCA
1701  GGACGGGGAA GTGATGGAGT ACACCACCAT CCTGCACCTC CGTCAGGTCA
1751  CTTTCGGGCA CGAGGGCCGC TACCAATGTG TCATCACCAA CCACTTTGGC
1801  TCCACCTATT CACATAAGGC CAGGCTCACC GTGAATGTGT TGCCATCATT
1851  CACCAAAACG CCCCACGACA TAACCATCCG GACCACCACC GTGGCCCGCC
1901  TCGAATGTGC TGCCACAGGT CACCCAAACC CTCAGATTGC CTGGCAGAAG
1951  GATGGAGGCA CGGATTTCCC CGCTGCCCGT GAGCGACGCA TGCATGTCAT
2001  GCCGGATGAC GACGTGTTTT TCATCACTGC TGTGAAAATA GATGACGCAG
2051  GGGTTTACAG CTGTACTGCT CAGAACTCAG CCGGTTCTAT TTCAGCTAAT
2101  GCCACCCTGA CTGTCCTAGA GACCCCATCC TTGGTGGTCC CCTTGGAAGA
2151  CCGTGTGGTA TCTGTGGGAG AAACAGTGGC CCTCCAATGC AAAGCCACGG
2201  GGAACCCTCC GCCCCGCATC ACCTGGTTCA AGGGGGACCG CCCGCTGAGC
2251  CTCACTGAGC GGCACCACCT GACCCCTGAC AACCAGCTCC TGGTGGTTCA
2301  GAACGTGGTG GCAGAGGATG CGGGCCGATA TACCTGTGAG ATGTCCAACA
2351  CCCTGGGCAC GGAGCGAGCT CACAGCCAGC TGAGCGTCCT GCCCGCAGCA
2401  GGCTGCAGGA AGGATGGGAC CACGGTAGGC ATCTTCACCA TTGCTGTCGT
2451  GAGCAGCATC GTCCTGACGT CACTGGTCTG GGTGTGCATC ATCTACCAGA
2501  CCAGGAAGAA GAGTGAAGAG TACAGTGTCA CCAACACAGA TGAAACCGTC
2551  GTGCCACCAG ATGTTCCAAG CTACCTCTCT TCTCAGGGGA CCCTTTCTGA
2601  CCGACAAGAA ACCGTGGTCA GGACCGAGGG TGGCCCTCAG GCCAATGGGC
2651  ACATTGAGAG CAATGGTGTG TGTCCAAGAG ATGCAAGCCA CTTTCCAGAG
2701  CCCGACACTC ACAGCGTTGC CTGCAGGCAG CCAAAGCTCT GTGCTGGGTC
2751  TGCGTATCAC AAAGAGCCGT GGAAAGCGAT GGAGAAAGCT GAAGGGACAC
2801  CTGGGCCACA TAAGATGGAA CACGGTGGCC GGGTCGTATG CAGTGACTGC
2851  AACACCGAAG TGGACTGTTA CTCCAGGGGA CAAGCCTTCC ACCCCCAGCC
2901  TGTGTCCAGA GACAGCGCAC AGCCAAGTGC GCCAAATGGC CCGGAGCCGG
2951  GTGGGAGTGA CCAAGAGCAT TCTCCACATC ACCAGTGCAG CAGGACTGCC
3001  GCTGGGTCCT GCCCCGAGTG CCAAGGGTCG CTCTACCCCA GTAACCACGA
3051  TAGAATGCTG ACGGCTGTGA AGAAAAAGCC AATGGCATCT CTAGATGGGA
3101  AAGGGGATTC TTCCTGGACT TTAGCAAGGT TGTATCACCC GGACTCCACA
3151  GAGCTACAGC CTGCATCTTC ATTAACTTCA GGCAGTCCAG AGCGCGCGGA
3201  AGCCCAGTAC TTGCTTGTTT CCAATGGCCA CCTCCCCAAA GCATGTGACG
3251  CCAGTCCCGA GTCCACGCCA CTGACAGGAC AGCTCCCCGG GAAACAGAGG
```

TABLE 1ᵃ-continued

```
3301  GTGCCACTGC TGTTGGCACC AAAAAGCTAG GTTTTGTCTA CCTCAGTTCT
3351  TGTCATACCA ATCTCTACGG GAAAGAGAGG TAGGAGAGGC TGCGAGGAAG
3401  CTTGGGTTCA AGCGTCACTC ATCTGTACAT AGTTGTAACT CCCATGTGGA
3451  GTATCAGTCG CTCACAGGAC TTGGATCTGA AGCACAGTAA ACGCAAGAGG
3501  GGATTTGTGT ACAAAAGGCA AAAAAAGTAT TTGATATCAT TGTACATAAG
3551  AGTTTTCAGA GATTTCATAT ATATCTTTTA CAGAGGCTAT TTTAATCTTT
3601  AGTGCATGGT TAACAGAAAA AAATTATACA ATTTTGACAA TATTATTTTT
3651  CGTATCAGGT TGCTGTTTAA TTTTGGAGGG GGTGGGGAAA TAGTTCTGGT
3701  GCCTTAACGC ATGGCTGGAA TTTATAGAGG CTACAACCAC ATTTGTTCAC
3751  AGGAGTTTTT GGTGCGGGGT GGGAAGGATG GAAGGCCTTG GATTTATATT
3801  GCACTTCATA GACCCCTAGG CTGCTGTGCG GTGGGACTCC ACATGCGCCG
3851  GAAGGAGCTT CAGGTGAGCA CTGCTCATGT GTGGATGCCC CTGCAACAGG
3901  CTTCCCTGTC TGTAGAGCCA GGGGTGCAAG TGCCATCCAC ACTTGCAGTG
3951  AATGGCTTTT CCTTTTAGGT TTAAGTCCTG TCTGTCTGTA AGGCGTAGAA
4001  TCTGTCCGTC TGTAAGGCGT AGAATGAGGG TTGTTAATCC ATCACAAGCA
4051  AAAGGTCAGA ACAGTTAAAC ACTGCCTTTC CTCCTCCTCT TATTTTATGA
4101  TAAAAGCAAA TGTGGCCTTC TCAGTATCAT TCGATTGCTA TTTGAGACTT
4151  TTAAATTAAG GTAAAGGCTG CTGGTGTTGG TACCTGTGGA TTTTTCTATA
4201  CTGATGTTTT CGTTTTGCCA ATATAATGAG TATTACATTG GCCTTGGGGG
4251  ACAGAAAGGA GGAAGTTCTG ACTTTTCAGG GCTACCTTAT TTCTACTAAG
4301  GACCCAGAGC AGGCCTGTCC ATGCCATTCC TTCGCACAAG ATGAAACTGA
4351  GCTGGGACTG GAAAGGACAG CCCTTGACCT GGGTTTCTGG GTATAATTTG
4401  CACTTTTGAG ACTGGTAGCT AACCATCTTA TGAGTGCCAA TGTGTCATTT
4451  AGTAAAACTT AAATAGAAAC AAGGTCCTTC AAATGTTCCT TTGGCCAAAA
4501  GCTGAAGGGA GTTACTGAGA AAATAGTTAA CAATTACTGT CAGGTGTCAT
4551  CACTGTTCAA AAGGTAAGCA CATTTAGAAT TTTGTTCTTG ACAGTTAACT
4601  GACTAATCTT ACTTCCACAA AATATGTGAA TTTGCTGCTT CTGAGAGGCA
4651  ATGTGAAAGA GGGAGTATTA CTTTTATGTA CAAAGTTATT TATTTATAGA
4701  AATTTTGGTA CAGTGTACAT TGAAAACCAT GTAAATATT GAAGTGTCTA
4751  ACAAATGGCA TTGAAGTGTC TTTAATAAAG GTTCATTTAT AAAAGTCAAA
4801  AAAAAAAAAA AAAAAAAAAA AAAAAAAAAA AAAAAAAAAA AAA
```

ᵃA nucleotide sequence of a human HLIG-1 (SEQ ID NO: 1).

TABLE 2ᵇ

```
  1  MARPVRGGLG APRRSPCLLL LWLLLLRLEP VTAAAGPRAP CAAACTCAGD
 51  PCTCAGDSLD CGGRGLAALP GDLPSWTRSL NLSYNKLAEI DPAGFEDLPN
101  LQEVYLNNHE LTAVASLGAG SSQVVALFLQ QQQNRSLDGS QLKAYLSLEV
151  LDLNLNNITE VRNTYFPHGP PIKELNLAGN RIGTLELGAF DGLSRSLLTL
201  RLSKNRITQL PVRAFKLPRL TQLDLNRNRI RLIEGLTFQG LNSLEVLKLQ
```

TABLE 2$^b$-continued

| | | | | |
|---|---|---|---|---|
| 251 | RNNISKLTDG | AFWGLSKMHV | LHLEYDSLVE | VNSGSLYGLT | ALHQLHLSNN |
| 301 | SIARIHRKGW | SFCQKLHELV | LSFNNLTRLD | EESLAELSSL | SVLRLSHNSI |
| 351 | SHIAEGAFKG | LRSLRVLDLD | HNEISGTIED | TSGAFSGLEF | GHSKLTLFGN |
| 401 | KIKSVAKRAF | SGLEGLEHLN | LGGNAIRSVG | FDAFVKMKNL | KELHISSDSF |
| 451 | LCDCQLKWLP | PWLIGRMLQA | FVTATCAHPE | SLKGQSIFSV | PPESFVCDDF |
| 501 | LKPQIITQPE | TTMAMVGKDI | RFTCSAASSS | SSPMTFAWKK | DNEVLTNADM |
| 551 | ENFVHVHAQD | GEVMEYTTIL | HLRQVTFGHE | GRYQCVITNH | FGSTYSHKAR |
| 601 | LTVNVLPSFT | KTPHDITIRT | TTVARLECAA | TGHPNPQIAW | QKDGGTDFPA |
| 651 | ARERRMHVMP | DDDVFFITDV | KIDDAGVYSC | TAQNSAGSIS | ANATLTVLET |
| 701 | PSLVVPLEDR | VVSVGETVAL | QCKATGNPPP | RITWFKGDRP | LSLTERHHLT |
| 751 | PDNQLLVVQN | VVAEDAGRYT | CEMSNTLGTE | RAHSQLSVLP | AAGCRKDGTT |
| 801 | VGIFTIAVVS | SIVLTSLVWV | CIIYQTRKKS | EEYSVTNTDE | TVVPPDVPSY |
| 851 | LSSQGTLSDR | QETVVRTEGG | PQANGHIESN | GVCPRDASHF | PEPDTHSVAC |
| 901 | RQPKLCAGSA | YHKEPWKAME | KAEGTPGPHK | MEHGGRVVCS | DCNTEVDCYS |
| 951 | RGQAFHPQPV | SRDSAQPSAP | NGPEPGGSDQ | EHSPHHQCSR | TAAGSCPECQ |
| 1001 | GSLYPSNHDR | MLTAVKKKPM | ASLDGKGDSS | WTLARLYHPD | STELQPASSL |
| 1051 | TSGSPERAEA | QYLLVSNGHL | PKACDASPES | TPLTGQLPGK | QRVPLLLAPK |
| 1101 | S | | | | |

$^b$An amino acid sequence of a human HLIG-1 (SEQ ID NO: 2).

One polynucleotide of the present invention encoding HLIG-1 may be obtained using standard cloning and screening, from a cDNA library derived from mRNA in cells of human brain, ovary, immune system, using the expressed sequence tag (EST) analysis (Adams, M. D., et al. *Science* (1991)252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding HLIG-1 polypeptide of SEQ ID NO:2 may be identical to the polypeptide encoding sequence contained in Table 1 (nucleotide number 25 to 3327 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of HLIG-1 polypeptide, the polynucleotide may include the coding sequence for the mature polypeptide or a fragment thereof, by itself, the coding sequence for the mature polypeptide or fragment in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding HLIG-1 variants comprising the amino acid sequence of HLIG-1 polypeptide of Table 2 (SEQ ID NO:2) in which several, 5–10, 1–5, 1–3, 1–2 or 1 amino acid residues are substituted, deleted or added, in any combination. Among the preferred polynucleotides of the present invention is contained in Table 3 (SEQ ID NO: 3) encoding the amino acid sequence of Table 4 (SEQ ID NO: 4).

TABLE 3$^c$

| | | | | |
|---|---|---|---|---|
| 1 | ACGCCCCACG | ACATAACCAT | CCGGACCACC | ACCGTGGCCC | GCCTCGAATG |
| 51 | TGCTGCCACA | GGTCACCCAA | ACCCTCAGAT | TGCCTGGCAG | AAGGATGGAG |
| 101 | GCACGGATTT | CCCCGCTGCC | CGTGAGCGAC | GCATGCATGT | CATGCCGGAT |
| 151 | GACGACGTGT | TTTTCATCAC | TGATGTGAAA | ATAGATGACG | CAGGGGTTTA |

TABLE 3ᶜ-continued

```
 201  CAGCTGTACT GCTCAGAACT CAGCCGGTTC TATTgnTACA GCTAATGCCA
 251  CCCTGACTGT CCTAGAGACC CCATCCTTGG TGGTCCCCTT GGAAGACCGT
 301  GTGGTATCTG TGGGAGAAAC AGTGGCCCTC CAATGCAAAG CCACGGGGAA
 351  CCCTCTGCCC CGCATCACCT GGTTCAAGGG GGACCTCCCG CTGAAGACCT
 401  GCACTGAGCC GGGCACCACT TGACCCCTGA CAACCAGCTC CTGGTGGTTC
 451  AGAACGTGGT GGGCAGAGGA TGCGGGCCGA TATACCTGTG AGATGTCCAA
 501  CACCCTGGGC ACGGAGCGAG CTCACAGTCC AGCTGAGCGT CCCTGCCCGC
 551  AGACAGGCTG CAGGTAAGGA TTGAACCAC GGTTGGCATC TTCCACCATT
 601  GACTGTCGTG AGCCAGCATC GTCCTGACGT CACTGGATCT GGGTTTGGA
 651  TTCATCTATC AGAACCAGGA AGAAGAGTGA AGAGTTACAG TTTTCCCCAC
 701  AACCAGGTTG AAAACCGTTG GTGGCACCAG ATGTTCCAAG CTACCTCTCT
 751  TCTCAGGGGA CCCTTTCTGA CCGACAAGAA ACCGTGGTCC AGGACCGAGG
 801  GTTCGGCCCT GAGGGCAATG GCACATTGA GAGCAATGGT GTGTGTCCAA
 851  GAGATGCAAG CCACTTTCCA GAGCCCGACA CTCACAGCGT TGCCTGCAGG
 901  CAGCCAAAGC TCTGTGCTGG GTCTGGGTAT CACAAAGAGC CGTGGAAAGC
 951  GATGGAGAAA GCTGGAAGGG ACACCTGGGC ACATGAAGA TGGGAAGACG
1001  GTGGACCGGG TCGTATGCAG TGACTGCAAC ACCGAAGTGG CAGAGACTGT
1051  TTACTCCAGG GGAACAAGCC TTCCACCCCC AGCCTGTGTC CAGAGGACAG
1101  TGCACAGCCA AGTGGGCCAA AATGGTCCCG GAGCCGGGTG GGGAAGTGAC
1151  CAAGAGGCAT TCTTCCACAT CACCATTGCA GAGGATTGCA CGTTGGGTCC
1201  TGCCCCGAGT GGCCCAGGGT TGTTTTTAAC CCCATTAACC ACGTTAGAAT
1251  GTTTTTTGAC GGTTTTTGAA GGAAAAGCCA TTGGCATCTC TAGATGGGAA
1301  AGGGGATTCT TCCTGGACTT TAGCAAGGTT GTATCACCCG GACTCCACAG
1351  AGCTACAGCC TGCATCTTCA TTAACTTCAG GCAGTCCAGA GCGCGCGGAA
1401  GCCCAGTACT TGCTTGTTTC CAATGGCCAC CTCCCCAAAG CATGTGACGC
1451  CAGTCCCGAG TCCACGCCAC TGACAGGACA GCTCCCCGGG AAACAGAGGG
1501  TGCCACTGCT GTTGGCACCA AAAAGCTAGG TTTTGTCTAC CTCAGTTCTT
1551  GGTCATACCA ATCTCTACGG GAAAGAGAGG TAGGAGAGGC TGCGAGGAAG
1601  CTTGGGTTCA AGCGTCACTC ATCTGTACAT AGTTGTAACT CCCATGTGGA
1651  GTATCCAGTC GTTCACAGGA CTTGGGATCT GAAGCACAGT AAACGCAAGA
1701  GGGGGATTTG TGTACCAAAA GGCAAAAAAA AGTATTTGAT ATCCATTGTA
1751  CCATAAGGGT TTTCAGGGGT TTCATATATA TCCTTTTAAC AGAGGTTATT
1801  TTAATCTTTA GTGCATGGTT AACCGGAAAA AATTTTTCCA TTTTGGCCAT
1851  TTTATTTTTC CGTATCCAGG TTGCTGTTTA ATTTGGAGG GGGTTGGGGA
1901  AATAGTTCTG GTGCCTTAAC GCATGGCTGG GAATTTATAG AGGCTACAAC
1951  CACATTTGTT CACAGGAAGT TTTTGGTGCG GGGTGGGAAG GATGGAAGGC
2001  CTTGGAATTT ATATTGCACT TCATAGACCC CTAGGCTGCT GTGCGGTGGG
2051  ACTCCACATG CGCCCGGAAG GAGCTTTCAG GTGAGCACTG CTCATGTGTG
2101  GATGCCCCTG CAACAGGCTT CCCTGTCTGT AGAGCCAGGG GTGCAAGTGC
2151  CCATCCACAC TTGCAGTGAA TGGCTTTTCC TTTTAGTTTT AAGTCCTGTC
```

TABLE 3[c]-continued

```
2201    TGTTTTTAAG GCGTAGGATT TGTCCTTCTG TAAGGCGTGG AATGAGGGTT

2251    GTTAATCCAT CACAAGCAAA AGGTCCGAAC CGTTAAACAC TGCCTTTCCT

2301    CCTCCTTATT TTGGTTCCCT TATTTTATGT TAAAAGCAAA TGTGGCCTTC

2351    TCAGTATCAT TCGATTGCTA TTTGAGACTT TTAAATTAAG GTAAAGGCTG

2401    CTGGTGTTGG TACCTGTGGA TTTTTCTATA CTGATGTTTT CGTTTTGCCA

2451    ATATAATGAG TATTACATTG GCCTTGGGGG ACAGAAAGGA GGAAGTTCTG

2501    ACTTTTCAGG GCTACCTTAT TTCTACTAAG GACCCAGAGC AGGCCTGTCC

2551    ATGCCATTCC TTCGCACAGA TGAAACTGAG CTGGGACTGG AAAGGACAGC

2601    CCTTGACCTG GGTTCTGGGT ATAATTTGCA CTTTTGAGAC TGGTAGCTAA

2651    CCATCTTATG AGTGCCAATG TGTCATTTAG TAAAACTTAA ATAGAAACAA

2701    GGTCCTTCAA ATGTTCCTTT GGCCAAAAGC TGAAGGGAGT TACTGAGAAA

2751    ATAGTTAACA ATTACTGTCA GGTGTCATCA CTGTTCAAAA GGTAAGCACA

2801    TTTAGAATTT TGTTCTTGAC AGTTAACTGA CTAATCTTAC TTCCACAAAA

2851    TATGTGAATT TGCTGCTTCT GAGAGGCAAT GTGAAAGAGG GAGTATTACT

2901    TTTATGTACA AAGTTATTTA TTTATAGAAA TTTTGGTACA GTGTACATTG

2951    AAAACCATGT AAAATATTGA AGTGTCTAAC AAATGGCATT GAAGTGTCTT

3001    TAATAAAGGT TCATTTATAA ATGTCAAAAT AANNNNAAGT TATTTATTTA

3051    TAGAAATTTT GGTACAGTGT ACATTGAAAA CCATGTAAAA TATTGAAGTG

3101    TNCTAACAAA TGGCATTGAA GTGTNCTTTA ATAAAGGTTC ATTTATAAAT

3151    GTCNNAAAA
```

[c]A partial nucleotide sequence of a human HLIG-1 (SEQ ID NO: 3).

TABLE 4[d]

```
  1     TPHDITIRTT TVARLECAAT GHPNPQIAWQ KDGGTDFPAA RERRMHVMPD

51     DDVFFITDVK IDDAGVYSCT AQNSAGSIXT ANATLTVLET PSLVVPLEDR

101     VVSVGETVAL QCKATGNPLP RITWFKGDLP LKTCTEPGTT
```

[d]A partial amino acid sequence of a human HLIG-1 (SEQ ID NO: 4).

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO:1 or a fragment thereof, may be used as hybridization probes for cDNA and genomic DNA, to isolate full-length cDNAs and genomic clones encoding HLIG-1 and to isolate cDNA and genomic clones of other genes (including genes encoding homologs and orthologs from species other than human) that have a high sequence similarity to the HLIG-1 gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding HLIG-1 polypeptide, including homologs and orthologs from species other than human, comprises the steps of screening an appropriate library under stingent hybridization conditions with a labeled probe having the SEQ ID NO:1 or a fragment thereof (including that of SEQ ID NO: 3), and isolating full-length cDNA and genomic clones containing said polynucleotide sequence. Such hybridization techniques are well known to those of skill in the art. Stringent hybridization conditions are as defined above or alternatively conditions under overnight incubation at 42° C. in a solution comprising: 50% formamide, 5× SSC (150 mM NaCl, 15 mM trisodium citrate), 50 mM sodium phosphate (pH7.6), 5× Denhardt's solution, 10% dextran sulfate, and 20 microgram/mil denatured, sheared salmon sperm DNA, followed by washing the filters in 0.1× SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY (1986) and Sambrook et al., MOLECULAR CLONING. A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, E. coli, Streptomyces and Bacillus subtilis cells; fungal cells, such as yeast cells and Aspergillus cells; insect cells such as Drosophila S2 and Spodoptera Sf9 cells; animal cells such as CHO, COS, HeLa, C 127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the HLIG-1 polypeptide is to be expressed for use in screening assays, generally, it is preferred that the polypeptide be produced at the surface of the cell. In this event, the cells may be harvested prior to use in the screening assay. If HLIG-1 polypeptide is secreted into the medium, the medium can be recovered in order to recover and purify the polypeptide; if produced intracellularly, the cells must first be lysed before the polypeptide is recovered.

HLIG-1 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of HLIG-1 polynucleotides for use as diagnostic reagents. Detection of a mutated form of HLIG-1 gene associated with a dysfunction will provide a diagnostic tool that can add to or define a diagnosis of a disease or susceptibility to a disease which results from under-expression, over-expression or altered expression of HLIG-1. Individuals carrying mutations in the HLIG-1 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled HLIG-1 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., Science (1985) 230:1242. Sequence changes at specific locations may also be revealed by nuclease protection assays, such as RNase and S1 protection or the chemical cleavage method. See Cotton et al., Proc Natl Acad Sci USA (1985) 85: 4397–4401. In another embodiment, an array of oligonucleotides probes comprising HLIG-1 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., Science, Vol 274, pp 610–613 (1996)).

The diagnostic assays offer a process for diagnosing or determining a susceptibility to neurological disorders such as Alzheimer's disease, multiple sclerosis and abnormal neural development; endocrine disorders such as diabetes; and heart disease through detection of mutation in the HLIG-1 gene by the methods described.

In addition, neurological disorders such as Alzheimer's disease, multiple sclerosis and abnormal neural development; endocrine disorders such as diabetes; and heart disease, can be diagnosed by methods comprising determining from a sample derived from a subject an abnormally decreased or increased level of HLIG-1 polypeptide or HLIG-1 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an HLIG-1, in a sample derived from a host are well-known to those of skill in the art. Such assay methods include radioimmunoassays, competitive-binding assays, Western Blot analysis and ELISA assays.

Thus in another aspect, the present invention relates to a diagonostic kit for a disease or suspectability to a disease, particularly neurological disorders such as Alzheimer's disease, multiple sclerosis and abnormal neural development; endocrine disorders such as diabetes; and heart disease, which comprises:

(a) a HLIG-1 polynucleotide, preferably the nucleotide sequence of SEQ ID NO: 1, or a fragment thereof;
(b) a nucleotide sequence complementary to that of (a);
(c) a HLIG-1 polypeptide, preferably the polypeptide of SEQ ID NO: 2, or a fragment thereof; or
(d) an antibody to a HLIG-1 polypeptide, preferably to the polypeptide of SEQ ID NO: 2. It will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the HLIG-1 polypeptides. The term "immunospecific" means that the antibodies have substantiall greater affinity for the polypeptides of the invention than their affinity for other related polypeptides in the prior art.

Antibodies generated against the HLIG-1 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., Nature (1975) 256:495497), the trioma technique, the human B-cell hybridoma technique (Kozbor et al., Immunology Today (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against HLIG-1 polypeptides may also be employed to treat neurological disorders such as Alzheimer's disease, multiple sclerosis and abnormal neural development; endocrine disorders such as diabetes; and heart disease, among others.

Vaccines

Another aspect of the invention relates to a method for inducing an immunological response in a mammal which comprises inoculating the mammal with HLIG-1 polypeptide, or a fragment thereof, adequate to produce antibody and/or T cell immune response to protect said animal from neurological disorders such as Alzheimer's disease, multiple sclerosis and abnormal neural development; endocrine disorders such as diabetes; and heart disease, among others. Yet another aspect of the invention relates to a method of inducing immunological response in a mammal which comprises, delivering HLIG-1 polypeptide via a vector directing expression of HLIG-1 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a HLIG-1 polypeptide wherein the composition comprises a HLIG-1 polypeptide or HLIG-1 gene. The vaccine formulation may further comprise a suitable carrier. Since HLIG-1 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The HLIG-1 polypeptide of the present invention may be employed in a screening process for compounds which bind the receptor and which activate (agonists) or inhibit activation of (antagonists) the receptor polypeptide of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al., *Current Protocols in Immunology* 1(2):Chapter 5 (1991).

HLIG-1 polypeptides are responsible for many biological functions, including many pathologies. Accordingly, it is desirous to find compounds and drugs which stimulate HLIG-1 on the one hand and which can inhibit the function of HLIG-1 on the other hand. In general, agonists are employed for therapeutic and prophylactic purposes for such conditions as neurological disorders such as Alzheimer's disease, multiple sclerosis and abnormal neural development; endocrine disorders such as diabetes; and heart disease. Antagonists may be employed for a variety of therapeutic and prophylactic purposes for such conditions as neurological disorders such as Alzheimer's disease, multiple sclerosis and abnormal neural development; endocrine disorders such as diabetes; and heart disease.

In general, such screening procedures involve producing appropriate cells which express the receptor polypeptide of the present invention on the surface thereof Such cells include cells from mammals, yeast, Drosophila or *E. coli*. Cells expressing the receptor (or cell membrane containing the expressed receptor) are then contacted with a test compound to observe binding, or stimulation or inhibition of a functional response.

The assays may simply test binding of a candidate compound wherein adherence to the cells bearing the receptor is detected by means of a label directly or indirectly associated with the candidate compound or in an assay involving competition with a labeled competitor. Further, these assays may test whether the candidate compound results in a signal generated by activation of the receptor, using detection systems appropriate to the cells bearing the receptor at their surfaces. Inhibitors of activation are generally assayed in the presence of a known agonist and the effect on activation by the agonist by the presence of the candidate compound is observed.

Further, the assays may simply comprise the steps of mixing a candidate compound with a solution containing a HLIG-1 polypeptide to form a mixture, measuring HLIG-1 activity in the mixture, and comparing the HLIG-1 activity of the mixture to a standard.

The HLIG-1 cDNA, protein and antibodies to the protein may also be used to configure assays for detecting the effect of added compounds on the production of HLIG-1 mRNA and protein in cells. For example, an ELISA may be constructed for measuring secreted or cell associated levels of HLIG-1 protein using monoclonal and polyclonal antibodies by standard methods known in the art, and this can be used to discover agents which may inhibit or enhance the production of HLIG-1 (also called antagonist or agonist, respectively) from suitably manipulated cells or tissues. Standard methods for conducting screening assays are well understood in the art.

Examples of potential HLIG-1 antagonists include antibodies or, in some cases, oligonucleotides or proteins which are closely related to the ligand of the HLIG-1, e.g., a fragment of the ligand, or small molecules which bind to the receptor but do not elicit a response, so that the activity of the receptor is prevented.

Thus in another aspect, the present invention relates to a screening kit for identifying agonists, antagonists, ligands, receptors, substrates, enzymes, etc. for HLIG-1 polypeptides; or compounds which decrease or enhance the production of HLIG-1 polypeptides, which comprises:

(a) a HLIG-1 polypeptide, preferably that of SEQ ID NO:2;
(b) a recombinant cell expressing a HLIG-1 polypeptide, preferably that of SEQ ID NO:2;
(c) a cell membrane expressing a HLIG-1 polypeptide; preferably that of SEQ ID NO: 2; or
(d) antibody to a HLIG-1 polypeptide, preferably that of SEQ ID NO: 2.

It will be appreciated that in any such kit, (a), (b), (c) or (d) may comprise a substantial component.

Prophylactic and Therapeutic Methods

This invention provides methods of treating an abnormal conditions related to both an excess of and insufficient amounts of HLIG-1 activity.

If the activity of HLIG-1 is in excess, several approaches are available. One approach comprises administering to a subject an inhibitor compound (antagonist) as hereinabove described along with a pharmaceutically acceptable carrier in an amount effective to inhibit activation by blocking binding of ligands to the HLIG-1, or by inhibiting a second signal, and thereby alleviating the abnormal condition.

In another approach, soluble forms of HLIG-1 polypeptides still capable of binding the ligand in competition with endogenous HLIG-1 may be administered. Typical embodiments of such competitors comprise fragments of the HLIG-1 polypeptide.

In still another approach, expression of the gene encoding endogenous HLIG-1 can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an under-expression of HLIG-1 and its activity, several approaches are also available. One approach comprises administering to a subject a therapeutically effective amount of a compound which activates HLIG-1, i.e., an agonist as described above, in combination with a pharmaceutically acceptable carrier, to thereby alleviate the abnormal condition. Alternatively, gene therapy may be employed to effect the endogenous production of HLIG-1 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996).

Formulation and Administration

Peptides, such as the soluble form of HLIG-1 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

Example 1

Cloning of the cDNA Containing the Complete Protein Coding Region

While there are several methods to obtain the full length cDNA, two are outlined below:

1) The method of Rapid Amplification of cDNA ENDS (RACE) can be utilized to extend the 5' end of incomplete cDNA clones (Frohman et al., Proc. Nat. Acad. Scd, USA 85, 8998–9002 (1988)). Briefly, a specific oligonucleotide complementary to the 5' region of the incomplete clone is annealed to mRNA and used to prime the synthesis of the cDNA strand. Following digestion of the mRNA with RNase H, a poly dC anchor segment is added to the 3' end of the extended cDNA and this region is then amplified by PCR using a set of nested primers positioned at the 5' end of the original cDNA, upstream of the cDNA primer, coupled with the anchor primer. The amplified fragment is cloned into an appropriate plasmid vector and subjected to restriction and sequence analysis. The linkage of the new 5' region with the original cDNA is confirmed by RT-PCR using primers positioned in the new 5' sequence coupled with primers in the original cDNA clone.

2) The polymerase chain reaction can be used to amplify the 5' end of the cDNA from human cDNA libraries using sequential rounds of nested PCR with two sets of primers. One set of antisense primers is specific to the 5' end of the partial cDNA and the other set of primers anneals to a vector specific sequence. The amplified products are cloned into an appropriate vector and subjected to restriction and sequence analysis. The linkage of the new and original sequences is confirmed as in (1) above.

For HLIG-1, most of the cDNA sequence was present in the cDNA clone defined by HGS EST: 231054. The missing 5' end of the 1.8 kb cDNA sequence was isolated by the 5' RACE PCR procedure, using mRNA from the human Daudi B cell line as the template. Assembly of these two DNA fragments generated the full length sequence of the HLIG-1 gene.

Example 2

HLIG-1 is the Human Homologue of Mouse LIG-1

As shown in the alignment below, the complete protein sequence of HLIG-1 exhibits 80.3% identity to the mouse LIG-1 protein and the homology extends throughout the entire protein sequence. This high linear homology demonstrates that HLIG-1 is the human homologue of mouse LIG-1. The extracellular domain contains 15 LRRs flanked by cysteine cluster regions, followed by 3 C2-type Ig-like domains.

```
                                                        NH2-Flanking              (SEQ ID NO:5)
HLIG-1    1  MARPVRGGLGAPRRSPCLLLLWLLLLRLEPVTAAAGPRAPCAAACTCAGDPCTCAGDSLD
             ||||  :|  ||||| :|   |||||||||  |:   :::||::|:   |:|    :::||||||:|||
MLIG-1    1  MARPGPGVLGAPRLAP-RLLLWLLLLLLQ-WPESAGAQARPRAPC---AAACTCAGNSLD LRR 1                          LRR 2
HLIG-1   61  CGGRGLAALPGDLPSWTRSLNLSYNKLAEIDPAGFEDLPNLQEVYLNNHELTAVASLGAG
             |:||||| :|| ||||||||||||||||:|||| :|:|||| :||||||||||:::||||::|||::
MLIG-1   56  CSGRGLATLPRDLPSWTRSLNLSYNRLSEIDSAAFEDLTNLQEVYLNSNELTAIPSLGTA LRR 3                          LRR 4
HLIG-1  121  SSQVVALFLQQQQNRSLDGSQLKAYLSLEVLDLNLNNITEVRNTYFPHGPPIKELNLAGN
             |    ||:||||:::    |:||||||:||||||||:  |||||:|:::||:|  :|:|||||:|
MLIG-1  116  SIGVVSLFLQHNKILSVDGSQLKSYLSLEVLDLSSNNITEIRSSCFPNGLRIRELNLASN

LRR 5                 LRR 6                 LRR 7
```

```
                                      -continued
HLIG-1  181  RIGTLELGAFDGLSRSLLTLRLSKNRITQLPVRAFKLPRLTQLDLNRNRIRLIEGLTFQG
             ||::||  ||||||||||||||||||||||||:||||||||||||||||||||||||||
MLIG-1  176  RISILESGAFDGLSRSLLTLRLSKNRITQLPVKAFKLPRLTQLDLNRNRIRLIEGLTGQG LRR 8                    LRR 9
HLIG-1  241  LNSLEVLKLQRNNISKLTDGAFWGLSKMHVLHLEYDSLVEVNSGSLYGLTALHQLHLSNN
             |:||||:|||||||:||||||||||||||||||:||||||||||||||||||||||||||
MLIG-1  236  LDSLEVLRLQRNNISRLTDGAFWGLSKMHVLHLEYNSLVEVNSGSLYGLTALHQLHLSNN LRR 10              LRR 11                 LRR 12
HLIG-1  301  SIARIHRKGWSFCQKLHELVLSFNNLTRLDEESLAELSSLSVLRLSHNSISHIAEGAFKG
             ||:||:|:|||||||||||:|||||||||||||||||||||:||||||:|||||||||||
MLIG-1  296  SISRIQRDGWSFCQKLHELILSFNNLTRLDEESLAELSSLSILRLSHNAISHIAEGAFKG LRR 13                      LRR 14
HLIG-1  361  LRSLRVLDLDHNEISGTIEDTSGAFSGLEFGHSKLTLFGNKIKSVAKRAFSGLEGLEHLN
             |:||||||||||||||||||||||:||: : ||||||||||||||||||||||:|||||
MLIG-1  356  LKSLRVLDLDHNEISGTIEDTSGAFTGLD-NLSKLTLFGNKIKSVAKRAFSGLESLEHLN LRR 15                   COOH-Flanking trailer
HLIG-1  421  LGGNAIRSVQFDAFVKMKNLKELHISSDSFLCDCQLKWLPPWLIGRMLQAFVTATCAHPE
             ||:|||||||||||:|||||||||:|||:|||||||||||||:||||||||||||||||
MLIG-1  415  LGENAIRSVQFDAFAKMKNLKELYISSESFLCDCQLKWLPPWLMGRMLQAFVTATCAHPE C2-type Ig-like domain I
HLIG-1  481  SLKGQSIFSVPPESFVCDDFLKPQIITQPETTMAMVGKDIRFTCSAASSSSSPMTFAWKK
             |||||||||  |:||||||| ||||||||||||||:||||||||||||||||||||||||
MLIG-1  475  SLKGQSIFSVLPDSFVCDDFPKPQIITQPETTMAVVGKDIRFTCSAASSSSSPMTFAWKK HLIG-1  541  DNEVLTNADMENFVHVHAQDGEVMEYTTILHLRQVTFGHEGRYQCVITNHFGSTYSHKAR
             |||||:||||||:|:||||||||||||||||||:|||||||||||:||||||||||||||
MLIG-1  535  DNEVLANADMENFAHVRAQDGEVMEYTTILHLRHVTFGHEGRYQCIITNHFGSTYSHKAR C2-type Ig-like domain II
HLIG-1  601  LTVNVLPSFTKTPHDITIRTTTVARLECAATGHPNPQIAWQKDGGTDFPAARARRMHVMP
             ||||||||||:||||:|||:|:|||||||||||||||||||||||||||||||:||||||
MLIG-1  595  LTVNVLPSFTKIPHDIAIRTGTTARLECAATGHPNPQIAWQKDGGTDFPAARERRMHVMP HLIG-1  661  DDDVFFITDVKIDDAGVYSCTAQNSAGSISANATLTVLETPSLVVPLEDRVVSVGETVAL
             |||||||||||||  |||||||||||||:|||||||||||||||:||||||:||||||:
MLIG-1  665  DDDVFFITDVKIDDMGVYSCTAQNSAGSVSANATLTVLETPSLAVPLEDRVVTVGETVAF C2-type Ig-like domain III
HLIG-1  721  QCKATGNPPPRITWFKGDRPLSLTERHHLTPDNQLLVVQNVVAEDAGRYTCEMSNTLGTE
             ||||||:|:|||||||:|||||||||||:|:|||||||||: :|||||||||||:||||
MLIG-1  715  QCKATGSPTPRITWLKGGRPLSLTERHHFTPGNQLLVVQNVMIDDAGRYTCEMSNPLGTE HLIG-1  781  RAHSQLSVLPAAGCRKDGTTVGIFTIAVVSSIVLTSLVWVCIIYQTRKKSEEYSVTNTDE
             ||||||:||::|||||||||||||||||||:|||||||||||||||||||||||||||||
MLIG-1  775  RAHSQLSILPTPGCRKDGTTVGIFTIAVVCSIVLTSLVWVCIIYQTRKKSEEYSVTNTDE HLIG-1  841  TVVPPDVPSYLSSQGTLSDRQETVVRTEGGPQANGHIESNGVCPRDASHFPEPDTHSVAC
             |:|||||||||||||||||||||||||||||:|||||||||| ||:| ||| |:||::|
MLIG-1  835  TIVPPDVPSYLSSQGTLSDRQETVVRTEGGHQANGHIESNGVCLRDPSLFPEVDIHSTTC HLIG-1  901  RQPKLCAGSAYHKEPWKAMEKAEGTPGPHKMEHGGRVVCSDCNTEVDCYSRGQAFHPQPV
             ||||||:|  |:||||:  |||:  |::||:  :|:|::||||:|::       |:||||
MLIG-1  895  RQPKLCVG--YTREPWKVTEKADRTAAPHTTAHSGAVCSDCSTDT-------AYHPQPV HLIG-1  961  SRDSAQPSAPNGPEPGGSDQEHSPHHQCSRTAAGSCPECQGSLYPSNHDRMLTAVKKKPM
             :|||:||:::::::|   |:|:|||||::| ||:||  : : |||||||||:|::::|:
MLIG-1  946  PRDSGQPGTASSQELRQHDREYSPHHPYSGTADGSHTLSGGSLYPSNHDRILPSLKNKA- HLIG-1  1021 ASLDGKGDSSWTLARLYHPDSTELQPASSLTSGSPE------RAEAQYLLVSNGHLPKAC
             ||  ||:|||||||:|:::|:::|:|:::|:||||        ::|||:|||||||||||
MLIG-1  1005 ASADGNGDSSWTLAKLHEADCIDLKPSPTLASGSPELMEDAISTEAQHLLVSNGHLPKAC HLIG-1  1075 DASPESTPLTGQLPGKQRVPLLLAPKS  (AA'S 1-1101 OF SEQ ID NO:2)
             |:||||:||:||::||:|  ||||||:|
MLIG-1  1065 DSSPESVPLKGQITGKRRGPLLLAPRS
```

Example 3

Homology with Other DNA and Protein Sequences

As noted above in the section "polynucleotides of the invention", the HLIG-1 protein shows homology to several other proteins. Proteins of identified function that show the closest homology are mammalian insulin binding protein acid labile subunit (IBP-ALS) and the drosophila proteins slit and peroxidasin (see the alignments below). This homology is primarily localized to the LRR region and is largely due to the consensus leucine and asparagine residues characteristic of LRRs. As noted in the background section, above, the structure of RI predicts that these consensus residues are not involved in ligand recognition and thus the observed homology is not a strong predictor of which proteins bind to HLIG-1.

Homology of Amino Acids 134–488 of SEQ ID NO:2 with IBP-ALS:

untranslated segment of CHOT1 and matches the antisense strand of human and mouse LIG-1 within the protein coding region.

```
HLIG-1  134  NRSLDGSQLKAYLSLEVLDLNLNNITEVRNTYFPHGPPI--KELNLAGNRIGTLELGAFD  191 (SEQ ID NO:6)
                 |::|::  |:  ::|  |:||:::::  :||:
ALS      36  AEGPQCPVACTCSHDDYTDELSVFCSSKNLTHLPDDIPVSTRALWLDGNNLSSIPSAAFQ   95

HLIG-1  192  GLSRSLLTLRLSKNRITQLPVRA-FKLPRLTQLDLNRNRIRLIEGLTFQGLNSLEVLKLQ  250
             :||  ||   |:|   :::    |  :|  :  |::|   |:|:|||:|  ::     |    ||: |:|
ALS      96  NLS-SLDFLNLQGSWLRSLEPQALLGLQNLYYLHLERNRLRNLAVGLFTHTPSLASLSLS  154

HLIG-1  251  RNNISKLTDGAFWGLSKMHVLHLEYDSLVEVNSGSLYGLTALHQLHLSNNSIARIHRKGW  310
             :|  :::|::|  |  |||::   |:|:::|||  :  ::  :  ||::||:|  |::|:::  :::
ALS     155  SNLLGRLEEGLFQGLSHLWDLNLGWNSLVVLPDTVFQGLGNLHELVLAGNKLTYLQPA--  212

HLIG-1  311  SFC--QKLHELVLSFNNLTRLDEESLAELSSLSVLRLSHNSISHIAEGAFKGLRSLRVLD  368
             ||     :|:||  ||  |:|  :::::  :::|::|     |  ||:|  |:  :|   |||  |:::||  ||
ALS     213  LFCGLGELRELDLSRNALRSVKANVFVHLPRLQKLYLDRNLITAVAPGAFLGMKALRWLD  272

HLIG-1  369  LDHNEISGTIEDTSGAFSGLEFGHSKLTLFGNKIKSVAKRAFSGLEGLEHLNLGGNAIRS  428
             |:||  ::|  :|||      |:||  :|      |   |   |:  |:|::|  ||:|||  |||
ALS     273  LSHNRVAGLMEDT---FPGL-LGLHVLRLAHNAIASLRPRTFKDLHFLEELQLGHNRIRQ  328

HLIG-1  429  VQFDAFVKMKNLKELHISSDSFLCDCQLKWLPPWLIGRMLQAFVTATCAHPESLKGQSIF  488
             :    :|    :  :|:   |    ::::
ALS     329  LGERTFEGLGQLEVLTLNDNQITEVRVGAFSGLFNVAVMNLSGNCLRSLRERVFQGLDKL  388
```

Homlogy of Amino Acids 268–506 of SEQ ID NO:2 with the drosophila protein slit:

```
HLIG-1  268  MHVLHLEYDSLVEVNSGSLYGLTALHQLHLSNNSIARIHRKGWSFCQKLHELVLSFNNLT  327  (SEQ ID NO:7)
                                |::::::::||    ::::::  | |    ||||
SLIT     57  GIHIPGGGVGVITEARCPRVCSCTGLNVDCSHRGLTSVPRK---ISADVERLELQGNNLT  113

HLIG-1  328  RLDEESLAELSSLSVLRLSHNSISHIAEGAFKGLRSLRVLDLDHNEISGTIEDTSGAFSG  387
             :  |::::  |::|::|:|::|      |:  ::|::|  ||    ||::|  |:::  ::  :|:|
SLIT    114  VIYETDFQRLTKLRMLQLTDNQIHTIERNSFQDLVSLERLDISNNVITTV---GRRVFKG  170

HLIG-1  388  LEFGHSKLTLFGNKIKSVAKRAFSGLEGLEHLNLGGNAIRSVQGDAFVKMKNLKELHISS  447
             :  :  ::|    |:|:|:::::::||:||    :||    :||    |:|::|::  :|    :  :  :::|:
SLIT    171  AQ-SLRSLQLDNNQITCLDEHAFKGLVELEILTLNNNNLTSLPHNIFGGLGRLRALRLSD  229

HLIG-1  448  DSFLCDCQLKWLPPWL-IGRMLQAFVTATCAHPESLKGQSIFSVPPESFVCDDFLKPQII  506
             ::|    |||:|:||:::|      :  :|:::    :  |:  |:  ||||::  :::  ::|    |:::
SLIT    230  NPFACDCHLSWLSRFLRSATRLAPY--TRCQSPSQLKGQNVADLHDQEFKCSGLTEHAPM  287
```

Homology of Amino Acids 188–367 of SEQ ID NO:2 with peroxidasin (POS):

```
HLIG-1  188  GAFDGLSRSLLTLRLSKNRITQLPVRAFKLPRLTQLDLNRNRIRLIEGLTFQGLNSLEVL  247  (SEQ ID NO:8)
             |:  :   |||:   ||||  |:    :|:  :|::|
POS      49  PGAGCPSRCLCFRTTVRCMHLLLEAVPAVAPQTSILDLRFNRIREIQPGAFRRLRNLNTL  108

HLIG-1  248  KLQRNNISKLTDGAFWGLSKMHVLHLEYDSLVEVNSGSLYGLTALHQLHLSNNSIARIHR  307
             |::|:|::::::|||   :|::::  |:|    :::  ::: ::  ||::|:||:|    |  |::  :
POS     109  LLNNNQIKRIPSGAFEDLENLKYLYLYKNEIQSIDRQAFKGLASLEQLYLHFNQIETLDP  168

HLIG-1  308  KGWSFCQKLHELVLSFNNLTRLDEESLAELSSLSVLRLSHNSISHIAEGAFKGLRSLRVL  367
             :::    :||:  |    |    |::|:|    :::::|:|::  |||:  |:::
POS     169  DSFQHLPKLERLFLHNNRITHLVPGTFNHLESMKRLRLDSNTLHCDCEILWLADLLKTYA  228
```

In nucleotide comparisons, the expected moderate sequence match was observed to IGP-ALS in the region of the LRRs. However, a surprisingly high homology (93% identity for murine LIG-1) was observed to rat CHOT1 mRNA which encodes a choline transporter that does not contain LRRs. This homology is artifactual, probably occurring during CHOT1 cloning, since it lies in the extreme 5'

Example 4

Tissue Expression Pattern of HLIG-1

Northern blot analysis of multiple human tissues shows that HLIG-1 is highly expressed in pancreas, brain, heart and skeletal muscle as a single transcript of approximately 5.0 kb.

All publications, including but not limited to patents and patent applications, cited in this specification are herein incorporated by reference as if each individual publication were specifically and individually indicated to be incorporated by reference herein as though fully set forth.

What is claimed is:

1. An isolated polynucleotide comprising a nucleotide sequence containing up to a total of 5 point mutations per 100 nucleotides of a polynucleotide sequence encoding the amino acid sequence set forth in SEQ ID NO:2, said point mutations being selected from the group consisting of single nucleotide deletions, single nucleotide additions, and single nucleotide substitutions.

2. The isolated polynucleotide of claim 1 wherein said polynucleotide comprises the nucleotide sequence set forth in SEQ ID NO:1 encoding the polypeptide having the amino acid sequence set forth in SEQ ID NO:2.

3. The isolated polynucleotide of claim 1 wherein said polynucleotide comprises a nucleotide sequence containing up to a total of 5 point mutations per 100 nucleotides of the nucleotide sequence set forth in SEQ ID NO:1, said point mutations being selected from the group consisting of single nucleotide deletions, single nucleotide additions, and single nucleotide substitutions.

4. The isolated polynucleotide of claim 3 wherein said nucleotide sequence comprises the nucleotide sequence set forth in SEQ ID NO: 1.

5. The isolated polynucleotide of claim 1 wherein the isolated polynucleotide is DNA or RNA.

6. An expression vector comprising an isolated DNA or RNA molecule encoding a polypeptide comprising an amino acid sequence containing up to a total of 5 point mutations per 100 amino acids of the amino acid sequence set forth in SEQ ID NO:2, said point mutations being selected from the group consisting of single amino acid deletions, single amino acid additions, and single amino acid substitutions.

7. An isolated host cell transformed with the expression vector of claim 6.

8. A process for producing a polypeptide having the amino acid sequence set forth in SEQ ID NO:2 comprising culturing the host cell of claim 7 under conditions sufficient for the production of said polypeptide and recovering said polypeptide from the culture.

9. A process for producing a recombinant host cell which produces a polypeptide having the amino acid sequence set forth in SEQ ID NO:2 comprising transforming or transfecting a host cell with the expression vector of claim 6 such that the host cell, under appropriate culture conditions, produces said polypeptide.

10. A recombinant host cell produced by the method of claim 9.

11. An isolated polynucleotide comprising a nucleotide sequence encoding the polypeptide having the amino acid sequence set forth in SEQ ID NO:2.

12. The isolated polynucleotide of claim 11 wherein said polynucleotide is RNA corresponding to the entire length of the polynucleotide set forth in SEQ ID NO:1.

13. The isolated polynucleotide of claim 11 wherein said polynucleotide is RNA corresponding to the entire coding region of the polynucleotide set forth in SEQ ID NO:1.

14. An isolated polynucleotide wherein said polynucleotide is fully complementary to the nucleotide sequence that encodes the polypeptide set forth in SEQ ID NO:2.

15. The isolated polynucleotide of claim 14 wherein said polynucleotide is fully complementary to the polynucleotide sequence set forth in SEQ ID NO:1.

16. An isolated polynucleotide encoding HLIG-1 polypeptide as shown in SEQ ID NO:2 except that 1–10 encoded amino acid residues are substituted, deleted, added, or any combination thereof.

* * * * *